United States Patent
Ong et al.

(10) Patent No.: US 10,934,533 B1
(45) Date of Patent: Mar. 2, 2021

(54) VARIANT DNA POLYMERASES HAVING IMPROVED PROPERTIES AND METHOD FOR IMPROVED ISOTHERMAL AMPLIFICATION OF A TARGET DNA

(71) Applicant: New England Biolabs, Inc., Ipswich, MA (US)

(72) Inventors: Jennifer Ong, Salem, MA (US); Nathan Tanner, West Newbury, MA (US); Yinhua Zhang, North Reading, MA (US); Yanxia Bei, Ipswich, MA (US); Vladimir Potapov, Auburndale, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 16/598,554

(22) Filed: Oct. 10, 2019

Related U.S. Application Data

(60) Provisional application No. 62/743,718, filed on Oct. 10, 2018.

(51) Int. Cl.
*C12N 9/12* (2006.01)
*C12N 7/00* (2006.01)

(52) U.S. Cl.
CPC ............ *C12N 9/1252* (2013.01); *C12N 7/00* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 6,627,424 B1 | 9/2003 | Wang | |
| 7,888,090 B2 | 2/2011 | Barnikow et al. | |
| 7,939,284 B2 | 5/2011 | Johnsson et al. | |
| 10,041,051 B2 | 8/2018 | Hsieh et al. | |
| 2010/0093555 A1 | 4/2010 | Bjornson et al. | |
| 2011/0003343 A1 | 1/2011 | Nikiforov et al. | |
| 2012/0034602 A1 | 2/2012 | Emig et al. | |
| 2014/0094375 A1 | 4/2014 | Kamtekar et al. | |
| 2014/0322759 A1 | 10/2014 | Skirgaila et al. | |
| 2015/0218535 A1* | 8/2015 | Kamtekar ........ | C12Y 207/0700 435/6.11 |
| 2015/0260680 A1 | 9/2015 | Davidson et al. | |
| 2016/0130644 A1 | 5/2016 | Menchen et al. | |
| 2017/0159033 A1 | 6/2017 | Kamtekar et al. | |

FOREIGN PATENT DOCUMENTS

| | | |
|---|---|---|
| WO | 2017109262 A1 | 6/2017 |
| WO | 2018118997 A2 | 6/2018 |
| WO | 2018191857 A1 | 10/2018 |
| WO | 2018195850 A1 | 11/2018 |

OTHER PUBLICATIONS

Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Accession Q37882. Dec. 15, 1998. (Year: 1998).*
Meijer et al Microbiol Mol Biol Rev 65: 261-287 (2001).
Fakruddin et al, J Pharm Bioallied Sci. 5: 245-252 (2013).
Garmendia et al, Journal of Biological Chemistry, 1992, 267, 2594-2599.
Esteban et al Journal of Biological Chemistry, 1993, 268, 2719-2726.
Dean et al., Genome Res. 11: 1095-1099 (2001).
Potapov et, al., Nucleic Acids Res 46(11):5753-5763 (2018).
De Vega, et al., PNAS, 107, 38:16506-16511 (2010).
Blanco, et al J Biol Chem. 1996 271:8509-12.
Kamtekar, et al., Mol Cell. 2004 16:609-18.
Berman, et al EMBO J. 2007 26: 3494-505.

* cited by examiner

*Primary Examiner* — Christian L Fronda
(74) *Attorney, Agent, or Firm* — New England Biolabs, Inc; Harriet M. Strimpel

(57) ABSTRACT

Variants of the bacteriophage B103 DNA polymerase are described herein. The variant has improved properties, that include when compared to wild-type Phi29 DNA polymerase, at least one of the following: increased thermostability, improved reaction rate for DNA amplification, reduced background and a reduction of bias. Methods of using the DNA polymerase variant are also described herein.

24 Claims, 9 Drawing Sheets

Specification includes a Sequence Listing.

```
                    121                                                          180
SEQ ID NO:1         KKLPFPVKKIAKDFKLTVLKGDIDYHKERPVGYKITPEEYAYIKNDIQIIAEALLIQFKQ
SEQ ID NO:2         KKLPFPVKKIAKDFQLPLLKGDIDYHAERPVGHEITPEEYEYIKNDIEIIARALDIQFKQ
SEQ ID NO:3         KKLPFPVKKIAKDFQLPLLKGDIDYHTERPVGHEITPEEYEYIKNDIEIIARALDIQFKQ
SEQ ID NO:4         KKLPFPVKKIAKDFQLPLLKGDIDYHTERPVGHEITPEEYEYIKNDIEIIARALDIQFKQ
SEQ ID NO:5         KKLPFPVKKIAKDFQLPLLKGDIDYHKERPVGHEITPEEYEYIKNDIEIIARALDIQFKQ
SEQ ID NO:6         KKLPFPVKKIAKDFQLPLLKGDIDYHKERPVGHEITPEEYEYIKNDIEIIARALDIQFKQ
SEQ ID NO:7         KKLPFPVKKIAKDFQLPLLKGDIDYHKERPVGHEITPEEYEYIKNDIEIIARALDIQFKQ
SEQ ID NO:8         KKLPFPVKKIAKDFQLPLLKGDIDYHIERPVGHEITPEEYEYIKNDIEIIARALDIQFKQ
SEQ ID NO:9         KKLPFPVKKIAKDFQLPLLKGDIDYHEERPVGHEITPEEYEYIKNDIEIIARALDIQFKQ
SEQ ID NO:10        KKLPFPVKKIAKDFQLPLLKGDIDYHGERPVGHEITPEEYEYIKNDIEIIARALDIQFKQ
SEQ ID NO:11        KKLPFPVKKIAKDFQLPLLKGDIDYHKERPVGHEITPEEYEYIKNDIEIIARALDIQFKQ
SEQ ID NO:12        KKLPFPVKKIAKDFQLPLLKGDIDYHGERPVGHEITPEEYEYIKNDIEIIARALDIQFKQ
SEQ ID NO:13        KKLPFPVKKIAKDFQLPLLKGDIDYHYERPVGHEITPEEYEYIKNDIEIIARALDIQFKQ
SEQ ID NO:14        KKLPFPVKKIAKDFQLPLLKGDIDYHYERPVGHEITPEEYEYIKNDIEIIARALDIQFKQ
SEQ ID NO:15        KKLPFPVKKIAKDFQLPLLKGDIDYHGERPVGHEITPEEYEYIKNDIEIIARALDIQFKQ
SEQ ID NO:16        KKLPFPVKKIAKDFQLPLLKGDIDYHKERPVGHEITPEEYEYIKNDIEIIARALDIQFKQ
SEQ ID NO:17        KKLPFPVKKIAKDFQLPLLKGDIDYHYERPVGHEITPEEYEYIKNDIEIIARALDIQFKQ
SEQ ID NO:18        KKLPFPVKKIAKDFQLPLLKGDIDYHYERPVGHEITPEEYEYIKNDIEIIARALDIQFKQ
SEQ ID NO:19        KKLPFPVKKIAKDFQLPLLKGDIDYHIERPVGHEITPEEYEYIKNDIEIIARALDIQFKQ
SEQ ID NO:20        KKLPFPVKKIAKDFQLPLLKGDIDYHIERPVGHEITPEEYEYIKNDIEIIARALDIQFKQ
SEQ ID NO:21        KKLPFPVKKIAKDFQLPLLKGDIDYHGERPVGHEITPEEYEYIKNDIEIIARALDIQFKQ
SEQ ID NO:22        KKLPFPVKKIAKDFQLPLLKGDIDYHIERPVGHEITPEEYEYIKNDIEIIARALDIQFKQ
SEQ ID NO:23        KKLPFPVKKIAKDFQLPLLKGDIDYHKERPVGHEITPEEYEYIKNDIEIIARALDIQFKQ
SEQ ID NO:24        KKLPFPVKKIAKDFQLPLLKGDIDYHEERPVGHEITPEEYEYIKNDIEIIARALDIQFKQ
SEQ ID NO:25        KKLPFPVKKIAKDFQLPLLKGDIDYHEERPVGHEITPEEYEYIKNDIEIIARALDIQFKQ
SEQ ID NO:26        KKLPFPVKKIAKDFQLPLLKGDIDYHIERPVGHEITPEEYEYIKNDIEIIARALDIQFKQ
SEQ ID NO:27        KKLPFPVKKIAKDFQLPLLKGDIDYHEERPVGHEITPEEYEYIKNDIEIIARALDIQFKQ 181                                                          240
SEQ ID NO:1         GLDRMTAGSDSLKGFKDIITTKKFKKVFPTLSLGLDKEVRYAYRGGFTWLNDRFKEKEIG
SEQ ID NO:2         GLDRMTAGSDSLKGFKDILSTKKFNKVFPKLSLPMDKEIRRAYRGGFTWLNDKYKEKEIG
SEQ ID NO:3         GLDRMTAGSDSLKGFKDILSTKKFNKVFPKLSLPMDKEIRKAYRGGFTWLNDKYKEKEIG
SEQ ID NO:4         GLDRMTAGSDSLKGFKDILSTKKFNKVFPKLSLPMDKEIRKAYRGGFTWLNDKYKEKEIG
SEQ ID NO:5         GLDRMTAGSDSLKGFKDILSTKKFNKVFPKLSLPMDKEIRYAYRGGFTWLNDKYKEKEIG
SEQ ID NO:6         GLDRMTAGSDSLKGFKDILSTKKFNKVFPKLSLPMDKEIRYAYRGGFTWLNDKYKEKEIG
SEQ ID NO:7         GLDRMTAGSDSLKGFKDILSTKKFNKVFPKLSLPMDKEIRGAYRGGFTWLNDKYKEKEIG
SEQ ID NO:8         GLDRMTAGSDSLKGFKDILSTKKFNKVFPKLSLPMDKEIRQAYRGGFTWLNDKYKEKEIG
SEQ ID NO:9         GLDRMTAGSDSLKGFKDILSTKKFNKVFPKLSLPMDKEIRQAYRGGFTWLNDKYKEKEIG
SEQ ID NO:10        GLDRMTAGSDSLKGFKDILSTKKFNKVFPKLSLPMDKEIRYAYRGGFTWLNDKYKEKEIG
SEQ ID NO:11        GLDRMTAGSDSLKGFKDILSTKKFNKVFPKLSLPMDKEIRHAYRGGFTWLNDKYKEKEIG
SEQ ID NO:12        GLDRMTAGSDSLKGFKDILSTKKFNKVFPKLSLPMDKEIRHAYRGGFTWLNDKYKEKEIG
SEQ ID NO:13        GLDRMTAGSDSLKGFKDILSTKKFNKVFPKLSLPMDKEIRGAYRGGFTWLNDKYKEKEIG
SEQ ID NO:14        GLDRMTAGSDSLKGFKDILSTKKFNKVFPKLSLPMDKEIRGAYRGGFTWLNDKYKEKEIG
SEQ ID NO:15        GLDRMTAGSDSLKGFKDILSTKKFNKVFPKLSLPMDKEIREAYRGGFTWLNDKYKEKEIG
SEQ ID NO:16        GLDRMTAGSDSLKGFKDILSTKKFNKVFPKLSLPMDKEIRAAYRGGFTWLNDKYKEKEIG
SEQ ID NO:17        GLDRMTAGSDSLKGFKDILSTKKFNKVFPKLSLPMDKEIRQAYRGGFTWLNDKYKEKEIG
SEQ ID NO:18        GLDRMTAGSDSLKGFKDILSTKKFNKVFPKLSLPMDKEIRAAYRGGFTWLNDKYKEKEIG
SEQ ID NO:19        GLDRMTAGSDSLKGFKDILSTKKFNKVFPKLSLPMDKEIRHAYRGGFTWLNDKYKEKEIG
SEQ ID NO:20        GLDRMTAGSDSLKGFKDILSTKKFNKVFPKLSLPMDKEIRAAYRGGFTWLNDKYKEKEIG
SEQ ID NO:21        GLDRMTAGSDSLKGFKDILSTKKFNKVFPKLSLPMDKEIRHAYRGGFTWLNDKYKEKEIG
SEQ ID NO:22        GLDRMTAGSDSLKGFKDILSTKKFNKVFPKLSLPMDKEIRYAYRGGFTWLNDKYKEKEIG
SEQ ID NO:23        GLDRMTAGSDSLKGFKDILSTKKFNKVFPKLSLPMDKEIRYAYRGGFTWLNDKYKEKEIG
SEQ ID NO:24        GLDRMTAGSDSLKGFKDILSTKKFNKVFPKLSLPMDKEIRHAYRGGFTWLNDKYKEKEIG
SEQ ID NO:25        GLDRMTAGSDSLKGFKDILSTKKFNKVFPKLSLPMDKEIRAAYRGGFTWLNDKYKEKEIG
SEQ ID NO:26        GLDRMTAGSDSLKGFKDILSTKKFNKVFPKLSLPMDKEIRNAYRGGFTWLNDKYKEKEIG
SEQ ID NO:27        GLDPMTAGSDSLKGFKDILSTKKFNKVFPKLSLPMDKEIRHAYRGGFTWLNDKYKEKEIG 241                                                          300
SEQ ID NO:1         EGMVFDVNSLYPAQMYSRLLPYGEPIVFEGKYVWDEDYPLHIQHIRCEFELKEGYIPTIQ
SEQ ID NO:2         EGMVFDVNSLYPSQMYSRPLPYGAPIVFQGKYEKDEQYPLYIQRIRFEFELKEGYIPTIQ
SEQ ID NO:3         EGMVFDVNSLYPSQMYSRPLPYGAPIVFQGKYEKDEQYPLYIQRIRFEFELKEGYIPTIQ
```

FIG. 6

```
SEQ ID NO:4     EGMVFDVNSLYPSQMYSRPLPYGAPIVFQGKYEKDEQYPLYIQRIRFEFELKEGYIPTIQ
SEQ ID NO:5     EGMVFDVNSLYPSQMYSRPLPYGAPIVFQGKYEKDEQYPLYIQRIRFEFELKEGYIPTIQ
SEQ ID NO:6     EGMVFDVNSLYPSQMYSRPLPYGAPIVFQGKYEKDEQYPLYIQRIRFEFELKEGYIPTIQ
SEQ ID NO:7     EGMVFDVNSLYPSQMYSRPLPYGAPIVFQGKYEKDEQYPLYIQRIRFEFELKEGYIPTIQ
SEQ ID NO:8     EGMVFDVNSLYPSQMYSRPLPYGAPIVFQGKYEKDEQYPLYIQRIRFEFELKEGYIPTIQ
SEQ ID NO:9     EGMVFDVNSLYPSQMYSRPLPYGAPIVFQGKYEKDEQYPLYIQRIRFEFELKEGYIPTIQ
SEQ ID NO:10    EGMVFDVNSLYPSQMYSRPLPYGAPIVFQGKYEKDEQYPLYIQRIRFEFELKEGYIPTIQ
SEQ ID NO:11    EGMVFDVNSLYPSQMYSRPLPYGAPIVFQGKYEKDEQYPLYIQRIRFEFELKEGYIPTIQ
SEQ ID NO:12    EGMVFDVNSLYPSQMYSRPLPYGAPIVFQGKYEKDEQYPLYIQRIRFEFELKEGYIPTIQ
SEQ ID NO:13    EGMVFDVNSLYPSQMYSRPLPYGAPIVFQGKYEKDEQYPLYIQRIRFEFELKEGYIPTIQ
SEQ ID NO:14    EGMVFDVNSLYPSQMYSRPLPYGAPIVFQGKYEKDEQYPLYIQRIRFEFELKEGYIPTIQ
SEQ ID NO:15    EGMVFDVNSLYPSQMYSRPLPYGAPIVFQGKYEKDEQYPLYIQRIRFEFELKEGYIPTIQ
SEQ ID NO:16    EGMVFDVNSLYPSQMYSRPLPYGAPIVFQGKYEKDEQYPLYIQRIRFEFELKEGYIPTIQ
SEQ ID NO:17    EGMVFDVNSLYPSQMYSRPLPYGAPIVFQGKYEKDEQYPLYIQRIRFEFELKEGYIPTIQ
SEQ ID NO:18    EGMVFDVNSLYPSQMYSRPLPYGAPIVFQGKYEKDEQYPLYIQRIRFEFELKEGYIPTIQ
SEQ ID NO:19    EGMVFDVNSLYPSQMYSRPLPYGAPIVFQGKYEKDEQYPLYIQRIRFEFELKEGYIPTIQ
SEQ ID NO:20    EGMVFDVNSLYPSQMYSRPLPYGAPIVFQGKYEKDEQYPLYIQRIRFEFELKEGYIPTIQ
SEQ ID NO:21    EGMVFDVNSLYPSQMYSRPLPYGAPIVFQGKYEKDEQYPLYIQRIRFEFELKEGYIPTIQ
SEQ ID NO:22    EGMVFDVNSLYPSQMYSRPLPYGAPIVFQGKYEKDEQYPLYIQRIRFEFELKEGYIPTIQ
SEQ ID NO:23    EGMVFDVNSLYPSQMYSRPLPYGAPIVFQGKYEKDEQYPLYIQRIRFEFELKEGYIPTIQ
SEQ ID NO:24    EGMVFDVNSLYPSQMYSRPLPYGAPIVFQGKYEKDEQYPLYIQRIRFEFELKEGYIPTIQ
SEQ ID NO:25    EGMVFDVNSLYPSQMYSRPLPYGAPIVFQGKYEKDEQYPLYIQRIRFEFELKEGYIPTIQ
SEQ ID NO:26    EGMVFDVNSLYPSQMYSRPLPYGAPIVFQGKYEKDEQYPLYIQRIRFEFELKEGYIPTIQ
SEQ ID NO:27    EGMVFDVNSLYPSQMYSRPLPYGAPIVFQGKYEKDEQYPLYIQRIRFEFELKEGYIPTIQ 301                                                        360
SEQ ID NO:1     IKRSRFYKGNEYLKSSGGEIADLWLSNVDLELMKEHYDLYNVEYISGLKFKATTGLFKDF
SEQ ID NO:2     IKKNPFFKGNEYLKNSGAEPVELYLTNVDLELIQEHYEMYNVEYIDGFKFREKTGLFKEF
SEQ ID NO:3     IKKNPFFKGNEYLKNSGVEPVELYLTNVDLELIQEHYELYNVEYIDGFKFREKTGLFKDF
SEQ ID NO:4     IKKNPFFKGNEYLKNSGVEPVELYLTNVDLELIQEHYELYNVEYIDGFKFREKTGLFKDF
SEQ ID NO:5     IKKNPFFKGNEYLKNSGGEPVELYLTNVDLELIQEHYELYNVEYIDGFKFREKTGLFKDF
SEQ ID NO:6     IKKNPFFKGNEYLKNSGGEPVELYLTNVDLELIQEHYELYNVEYIDGFKFREKTGLFKDF
SEQ ID NO:7     IKKNPFFKGNEYLKNSGEEPVELYLTNVDLELIQEHYEVYNVEYIDGFKFREKTGLFKNF
SEQ ID NO:8     IKKNPFFKGNEYLKNSGTEPVELYLTNVDLELIQEHYEIYNVEYIDGFKFREKTGLFKTF
SEQ ID NO:9     IKKNPFFKGNEYLKNSGGEPVELYLTNVDLELIQEHYEIYNVEYIDGFKFREKTGLFKTF
SEQ ID NO:10    IKKNPFFKGNEYLKNSGNEPVELYLTNVDLELIQEHYEIYNVEYIDGFKFREKTGLFKTF
SEQ ID NO:11    IKKNPFFKGNEYLKNSGDEPVELYLTNVDLELIQEHYELYNVEYIDGFKFREKTGLFKNF
SEQ ID NO:12    IKKNPFFKGNEYLKNSGNEPVELYLTNVDLELIQEHYEIYNVEYIDGFKFREKTGLFKTF
SEQ ID NO:13    IKKNPFFKGNEYLKNSGDEPVELYLTNVDLELIQEHYEVYNVEYIDGFKFREKTGLFKNF
SEQ ID NO:14    IKKNPFFKGNEYLKNSGTEPVELYLTNVDLELIQEHYEIYNVEYIDGFKFREKTGLFKNF
SEQ ID NO:15    IKKNPFFKGNEYLKNSGTEPVELYLTNVDLELIQEHYELYNVEYIDGFKFREKTGLFKNF
SEQ ID NO:16    IKKNPFFKGNEYLKNSGEEPVELYLTNVDLELIQEHYEIYNVEYIDGFKFREKTGLFKQF
SEQ ID NO:17    IKKNPFFKGNEYLKNSGDEPVELYLTNVDLELIQEHYELYNVEYIDGFKFREKTGLFKDF
SEQ ID NO:18    IKKNPFFKGNEYLKNSGEEPVELYLTNVDLELIQEHYELYNVEYIDGFKFREKTGLFKNF
SEQ ID NO:19    IKKNPFFKGNEYLKNSGGEPVELYLTNVDLELIQEHYEVYNVEYIDGFKFREKTGLFKNF
SEQ ID NO:20    IKKNPFFKGNEYLKNSGGEPVELYLTNVDLELIQEHYEIYNVEYIDGFKFREKTGLFKTF
SEQ ID NO:21    IKKNPFFKGNEYLKNSGDEPVELYLTNVDLELIQEHYELYNVEYIDGFKFREKTGLFKNF
SEQ ID NO:22    IKKNPFFKGNEYLKNSGDEPVELYLTNVDLELIQEHYEVYNVEYIDGFKFREKTGLFKNF
SEQ ID NO:23    IKKNPFFKGNEYLKNSGEEPVELYLTNVDLELIQEHYELYNVEYIDGFKFREKTGLFKTF
SEQ ID NO:24    IKKNPFFKGNEYLKNSGGEPVELYLTNVDLELIQEHYEVYNVEYIDGFKFREKTGLFKDF
SEQ ID NO:25    IKKNPFFKGNEYLKNSGTEPVELYLTNVDLELIQEHYEIYNVEYIDGFKFREKTGLFKNF
SEQ ID NO:26    IKKNPFFKGNEYLKNSGTEPVELYLTNVDLELIQEHYEVYNVEYIDGFKFREKTGLFKNF
SEQ ID NO:27    IKKNPFFKGNEYLKNSGDEPVELYLTNVDLELIQEHYEVYNVEYIDGFKFREKTGLFKTF 361                                                        420
SEQ ID NO:1     IDKWTYIKTTSEGAIKQLAKLMLNSLYGKFASNPDVTGKVPYLKENGALGFRLGEEETKD
SEQ ID NO:2     IDKWTYVKTHEKGAKKQLAKLMFDSLYGKFASNPDVTGKVPYLKEDGSLGFRVGDEEYKD
SEQ ID NO:3     IDKWTYVKTHEEGAKKQLAKLMLNSLYGKFASNPDVTGKVPYLKDDGSLGFRVGDEEYKD
SEQ ID NO:4     IDKWTYVKTHEEGAKKQLAKLMLNSLYGKFASNPDVTGKVPYLKDDGSLGFRVGDEEYKD
SEQ ID NO:5     IDKWTYVKTHEEGAKKQLAKLMLNSLYGKFASNPDVTGKVPYLKEDGSLGFRVGDEEYKD
SEQ ID NO:6     IDKWTYVKTHEEGAKKQLAKLMLNSLYGKFASNPDVTGKVPYLKEDGSLGFRVGDEEYKD
SEQ ID NO:7     IDKWTYVKTHENGAKKQLAKLMFDSLYGKFASNPDVTGKVPYLKEDGSLGFRVGDEEYKD
SEQ ID NO:8     IDKWTYVKTHENGAKKQLAKLMFDSLYGKFASNPDVTGKVPYLKEDGSLGFRVGDEEYKD
```

FIG. 6 (Cont.)

```
SEQ ID NO:9     IDKWTYVKTHETGAKKQLAKLMFDSLYGKFASNPDVTGKVPYLKEDGSLGFRVGDEEYKD
SEQ ID NO:10    IDKWTYVKTHENGAKKQLAKLMFDSLYGKFASNPDVTGKVPYLKEDGSLGFRVGDEEYKD
SEQ ID NO:11    IDKWTYVKTHETGAKKQLAKLMFDSLYGKFASNPDVTGKVPYLKEDGSLGFRVGDEEYKD
SEQ ID NO:12    IDKWTYVKTHEEGAKKQLAKLMFDSLYGKFASNPDVTGKVPYLKEDGSLGFRVGDEEYKD
SEQ ID NO:13    IDKWTYVKTHETGAKKQLAKLMFDSLYGKFASNPDVTGKVPYLKEDGSLGFRVGDEEYKD
SEQ ID NO:14    IDKWTYVKTHETGAKKQLAKLMFDSLYGKFASNPDVTGKVPYLKEDGSLGFRVGDEEYKD
SEQ ID NO:15    IDKWTYVKTHENGAKKQLAKLMFDSLYGKFASNPDVTGKVPYLKEDGSLGFRVGDEEYKD
SEQ ID NO:16    IDKWTYVKTHEEGAKKQLAKLMFDSLYGKFASNPDVTGKVPYLKEDGSLGFRVGDEEYKD
SEQ ID NO:17    IDKWTYVKTHETGAKKQLAKLMFDSLYGKFASNPDVTGKVPYLKEDGSLGFRVGDEEYKD
SEQ ID NO:18    IDKWTYVKTHEEGAKKQLAKLMFDSLYGKFASNPDVTGKVPYLKEDGSLGFRVGDEEYKD
SEQ ID NO:19    IDKWTYVKTHENGAKKQLAKLMFDSLYGKFASNPDVTGKVPYLKEDGSLGFRVGDEEYKD
SEQ ID NO:20    IDKWTYVKTHENGAKKQLAKLMFDSLYGKFASNPDVTGKVPYLKEDGSLGFRVGDEEYKD
SEQ ID NO:21    IDKWTYVKTHENGAKKQLAKLMFDSLYGKFASNPDVTGKVPYLKEDGSLGFRVGDEEYKD
SEQ ID NO:22    IDKWTYVKTHETGAKKQLAKLMFDSLYGKFASNPDVTGKVPYLKEDGSLGFRVGDEEYKD
SEQ ID NO:23    IDKWTYVKTHETGAKKQLAKLMFDSLYGKFASNPDVTGKVPYLKEDGSLGFRVGDEEYKD
SEQ ID NO:24    IDKWTYVKTHETGAKKQLAKLMFDSLYGKFASNPDVTGKVPYLKEDGSLGFRVGDEEYKD
SEQ ID NO:25    IDKWTYVKTHENGAKKQLAKLMFDSLYGKFASNPDVTGKVPYLKEDGSLGFRVGDEEYKD
SEQ ID NO:26    IDKWTYVKTHETGAKKQLAKLMFDSLYGKFASNPDVTGKVPYLKEDGSLGFRVGDEEYKD
SEQ ID NO:27    IDKWTYVKTHETGAKKQLAKLMFDSLYGKFASNPDVTGKVPYLKEDGSLGFRVGDEEYKD 421                                                        480
SEQ ID NO:1     PVYTPMGVFITAWARYTTITAAQACYDRIIYCDTDSIHLTGTEIPDVIKDIVDPKKLGYW
SEQ ID NO:2     PVYTPMGVFITAWARFTTITAAQACYDRIIYCDTDSIHLTGTEVPEIIKDIVDPKKLGYW
SEQ ID NO:3     PVYTPMGVFITAWARFTTITAAQACYDRIIYCDTDSIHLTGTEVPEIIKDIVDPKKLGYW
SEQ ID NO:4     PVYTPMGVFITAWARFTTITAAQACYDRIIYCDTDSIHLTGTEVPEIIKDIVDPKKLGYW
SEQ ID NO:5     PVYTPMGVFITAWARFTTITAAQACYDRIIYCDTDSIHLTGTEVPEIIKDIVDPKKLGYW
SEQ ID NO:6     PVYTPMGVFITAWARFTTITAAQACYDRIIYCDTDSIHLTGTEVPEIIKDIVDPKKLGYW
SEQ ID NO:7     PVYTPMGVFITAWARFTTITAAQACYDRIIYCDTDSIHLTGTEVPEIIKDIVDPKKLGYW
SEQ ID NO:8     PVYTPMGVFITAWARFTTITAAQACYDRIIYCDTDSIHLTGTEVPEIIKDIVDPKKLGYW
SEQ ID NO:9     FVYTPMGVFITAWARFTTITAAQACYDRIIYCDTDSIHLTGTEVPEIIKDIVDPKKLGYW
SEQ ID NO:10    PVYTPMGVFITAWARFTTITAAQACYDRIIYCDTDSIHLTGTEVPEIIKDIVDPKKLGYW
SEQ ID NO:11    PVYTPMGVFITAWARFTTITAAQACYDRIIYCDTDSIHLTGTEVPEIIKDIVDPKKLGYW
SEQ ID NO:12    PVYTPMGVFITAWARFTTITAAQACYDRIIYCDTDSIHLTGTEVPEIIKDIVDPKKLGYW
SEQ ID NO:13    PVYTPMGVFITAWARFTTITAAQACYDRIIYCDTDSIHLTGTEVPEIIKDIVDPKKLGYW
SEQ ID NO:14    PVYTPMGVFITAWARFTTITAAQACYDRIIYCDTDSIHLTGTEVPEIIKDIVDPKKLGYW
SEQ ID NO:15    FVYTPMGVFITAWARFTTITAAQACYDRIIYCDTDSIHLTGTEVPEIIKDIVDPKKLGYW
SEQ ID NO:16    PVYTPMGVFITAWARFTTITAAQACYDRIIYCDTDSIHLTGTEVPEIIKDIVDPKKLGYW
SEQ ID NO:17    PVYTPMGVFITAWARFTTITAAQACYDRIIYCDTDSIHLTGTEVPEIIKDIVDPKKLGYW
SEQ ID NO:18    PVYTPMGVFITAWARFTTITAAQACYDRIIYCDTDSIHLTGTEVPEIIKDIVDPKKLGYW
SEQ ID NO:19    PVYTPMGVFITAWARFTTITAAQACYDRIIYCDTDSIHLTGTEVPEIIKDIVDPKKLGYW
SEQ ID NO:20    PVYTPMGVFITAWARFTTITAAQACYDRIIYCDTDSIHLTGTEVPEIIKDIVDPKKLGYW
SEQ ID NO:21    PVYTPMGVFITAWARFTTITAAQACYDRIIYCDTDSIHLTGTEVPEIIKDIVDPKKLGYW
SEQ ID NO:22    PVYTPMGVFITAWARFTTITAAQACYDRIIYCDTDSIHLTGTEVPEIIKDIVDPKKLGYW
SEQ ID NO:23    FVYTPMGVFITAWARFTTITAAQACYDRIIYCDTDSIHLTGTEVPEIIKDIVDPKKLGYW
SEQ ID NO:24    PVYTPMGVFITAWARFTTITAAQACYDRIIYCDTDSIHLTGTEVPEIIKDIVDPKKLGYW
SEQ ID NO:25    PVYTPMGVFITAWARFTTITAAQACYDRIIYCDTDSIHLTGTEVPEIIKDIVDPKKLGYW
SEQ ID NO:26    PVYTPMGVFITAWARFTTITAAQACYDRIIYCDTDSIHLTGTEVPEIIKDIVDPKKLGYW
SEQ ID NO:27    PVYTPMGVFITAWARFTTITAAQACYDRIIYCDTDSIHLTGTEVPEIIKDIVDPKKLGYW 481                                                        540
SEQ ID NO:1     AHESTFKRAKYLRQKTYIQDIYMKEVDGKLVEGSPDDYTDIKFSVKCAGMTDKIKKEVTF
SEQ ID NO:2     AHESTFKRAKYLRQKTYIQDIYAKEVDGKLIECSPDEATTTKFSVKCAGMTDTIKKKVTF
SEQ ID NO:3     AHESTFKRAKYLRQKTYIQDIYVKEVDGKLKECSPDEATTTKFSVKCAGMTDTIKKKVTF
SEQ ID NO:4     AHESTFKRAKYLRQKTYIQDIYMKEVDGKLVECSPDEATTTKFSVKCAGMTDTIKKKVTF
SEQ ID NO:5     AHESTFKRAKYLRQKTYIQDIYMKEVDGKLVECSPDEATTTKFSVKCAGMTDTIKKKVTF
SEQ ID NO:6     AHESTFKRAKYLRQKTYIQDIYMKEVDGKLVECSPDEATTTKFSVKCAGMTDTIKKKVTF
SEQ ID NO:7     AHESTFKRAKYLRQKTYIQDIYKKEVDGKLGECSPDEATTTKFSVKCAGMTDTIKKKVTF
SEQ ID NO:8     AHESTFKRAKYLRQKTYIQDIYKKEVDGKLRECSPDEATTTKFSVKCAGMTDTIKKKVTF
SEQ ID NO:9     AHESTFKRAKYLRQKTYIQDIYGKEVDGKLDECSPDEATTTKFSVKCAGMTDTIKKKVTF
SEQ ID NO:10    AHESTFKRAKYLRQKTYIQDIYKKEVDGKLRECSPDEATTTKFSVKCAGMTDTIKKKVTF
SEQ ID NO:11    AHESTFKRAKYLRQKTYIQDIYKKEVDGKLGECSPDEATTTKFSVKCAGMTDTIKKKVTF
SEQ ID NO:12    AHESTFKRAKYLRQKTYIQDIYMKEVDGKLRECSPDEATTTKFSVKCAGMTDTIKKKVTF
SEQ ID NO:13    AHESTFKRAKYLRQKTYIQDIYKKEVDGKLVECSPDEATTTKFSVKCAGMTDTIKKKVTF
```

FIG. 6 (Cont.)

```
SEQ ID NO:14   AHESTFKRAKYLRQKTYIQDIYKKEVDGKLRECSPDEATTTKFSVKCAGMTDTIKKKVTF
SEQ ID NO:15   AHESTFKRAKYLRQKTYIQDIYKKEVDGKLRECSPDEATTTKFSVKCAGMTDTIKKKVTF
SEQ ID NO:16   AHESTFKRAKYLRQKTYIQDIYMKEVDGKLGECSPDEATTTKFSVKCAGMTDTIKKKVTF
SEQ ID NO:17   AHESTFKRAKYLRQKTYIQDIYGKEVDGKLVECSPDEATTTKFSVKCAGMTDTIKKKVTF
SEQ ID NO:18   AHESTFKRAKYLRQKTYIQDIYMKEVDGKLVECSPDEATTTKFSVKCAGMTDTIKKKVTF
SEQ ID NO:19   AHESTFKRAKYLRQKTYIQDIYMKEVDGKLGECSPDEATTTKFSVKCAGMTDTIKKKVTF
SEQ ID NO:20   AHESTFKRAKYLRQKTYIQDIYMKEVDGKLDECSPDEATTTKFSVKCAGMTDTIKKKVTF
SEQ ID NO:21   AHESTFKRAKYLRQKTYIQDIYMKEVDGKLGECSPDEATTTKFSVKCAGMTDTIKKKVTF
SEQ ID NO:22   AHESTFKRAKYLRQKTYIQDIYMKEVDGKLDECSPDEATTTKFSVKCAGMTDTIKKKVTF
SEQ ID NO:23   AHESTFKRAKYLRQKTYIQDIYGKEVDGKLGECSPDEATTTKFSVKCAGMTDTIKKKVTF
SEQ ID NO:24   AHESTFKRAKYLRQKTYIQDIYGKEVDGKLDECSPDEATTTKFSVKCAGMTDTIKKKVTF
SEQ ID NO:25   AHESTFKRAKYLRQKTYIQDIYGKEVDGKLVECSPDEATTTKFSVKCAGMTDTIKKKVTF
SEQ ID NO:26   AHESTFKRAKYLRQKTYIQDIYGKEVDGKLVECSPDEATTTKFSVKCAGMTDTIKKKVTF
SEQ ID NO:27   AHESTFKRAKYLRQKTYIQDIYMKEVDGKLVECSPDEATTTKFSVKCAGMTDTIKKKVTF 541                            572
SEQ ID NO:1    ENFKVGFSRKMKPKPVQVPGGVVLVDDTFTIK
SEQ ID NO:2    DNFRVGFSSTGKPKPVQVNGGVVLVDSVFTIK
SEQ ID NO:3    DNFAVGFSSMGKPKPVQVNGGVVLVDSVFTIK
SEQ ID NO:4    DNFAVGFSSMGKPKPVQVNGGVVLVDSVFTIK
SEQ ID NO:5    DNFKVGFSSKGKPKPVQVNGGVVLVDSVFTIK
SEQ ID NO:6    DNFKVGFSRSGKPKPVQVNGGVVLVDSVFTIK
SEQ ID NO:7    DNFQVGFSSNGKPKPVQVNGGVVLVDSVFTIK
SEQ ID NO:8    DNFQVGFSSKGKPKPVQVNGGVVLVDSVFTIK
SEQ ID NO:9    DNFKVGFSSKGKPKPVQVNGGVVLVDSVFTIK
SEQ ID NO:10   DNFEVGFSSDGKPKPVQVNGGVVLVDSVFTIK
SEQ ID NO:11   DNFDVGFSSSGKPKPVQVNGGVVLVDSVFTIK
SEQ ID NO:12   DNFEVGFSSSGKPKPVQVNGGVVLVDSVFTIK
SEQ ID NO:13   DNFKVGFSSEGKPKPVQVNGGVVLVDSVFTIK
SEQ ID NO:14   DNFHVGFSSKGKPKPVQVNGGVVLVDSVFTIK
SEQ ID NO:15   DNFHVGFSSKGKPKPVQVNGGVVLVDSVFTIK
SEQ ID NO:16   DNFDVGFSSKGKPKPVQVNGGVVLVDSVFTIK
SEQ ID NO:17   DNFDVGFSSDGKPKPVQVNGGVVLVDSVFTIK
SEQ ID NO:18   DNFNVGFSSNGKPKPVQVNGGVVLVDSVFTIK
SEQ ID NO:19   DNFKVGFSSNGKPKPVQVNGGVVLVDSVFTIK
SEQ ID NO:20   DNFNVGFSSSGKPKPVQVNGGVVLVDSVFTIK
SEQ ID NO:21   DNFQVGFSSDGKPKPVQVNGGVVLVDSVFTIK
SEQ ID NO:22   DNFHVGFSSNGKPKPVQVNGGVVLVDSVFTIK
SEQ ID NO:23   DNFEVGFSSNGKPKPVQVNGGVVLVDSVFTIK
SEQ ID NO:24   DNFDVGFSSDGKPKPVQVNGGVVLVDSVFTIK
SEQ ID NO:25   DNFKVGFSSNGKPKPVQVNGGVVLVDSVFTIK
SEQ ID NO:26   DNFEVGFSSKGKPKPVQVNGGVVLVDSVFTIK
SEQ ID NO:27   DNFNVGFSSEGKPKPVQVNGGVVLVDSVFTIK
```

FIG. 6 (Cont.)

VARIANT DNA POLYMERASES HAVING IMPROVED PROPERTIES AND METHOD FOR IMPROVED ISOTHERMAL AMPLIFICATION OF A TARGET DNA

CROSS REFERENCE

This application claims priority to U.S. Provisional Patent Application No. 62/743,718 filed Oct. 10, 2018, herein incorporated by reference.

BACKGROUND

Members of the Phi29 family of DNA polymerases, such as the polymerases from bacteriophage Phi29, B103, M2(Y) and Nf, do not need accessory proteins and possess a number of distinctive biochemical properties including a strong binding capacity for single stranded DNA, strand displacement activity, high processivity and a proofreading activity (see, e.g., Meijer et al Microbiol Mol Biol Rev. 65: 261-287 (2001)). These properties make these DNA polymerases suitable in a variety of applications, including rolling circle amplification (RCA), multiple strand displacement amplification (MDA) and whole genome amplification (WGA) (see, e.g., Fakruddin et al, J Pharm Bioallied Sci. 5: 245-252 (2013)). The DNA polymerase of bacteriophage Phi29 from *Bacillus subtilis* is a well-studied example of this class of polymerases (see, e.g., Garmendia et al, Journal of Biological Chemistry, 267, 2594-2599 (1992) and Esteban et al Journal of Biological Chemistry, 268, 2719-2726 (1993)).

There is a continued need for modified polymerases that have improved properties with respect to amplifying DNA. Desirable improved properties may include any one or more of the following: improved efficiency of polymerase activity, specificity and accuracy, yield, reduced sequence bias, reduction in non-template amplification; and capability of working well at elevated temperatures and/or high salt conditions.

SUMMARY

In one embodiment, the composition has (a) an amino acid sequence that has at least 95% sequence identity with SEQ ID NO:2; and (b) one or more amino acid substitutions at positions selected from the group consisting of positions 147, 221, 318, 339, 359, 372, 503, 511, 544, 550, wherein, in the polymerase: the amino acid at a position 147 is not alanine or threonine, the amino acid at a position 221 is not arginine or lysine, the amino acid at a position 318 is not alanine or valine, the amino acid at a position 339 is not methionine, the amino acid at a position 359 is not glutamic acid, the amino acid at a position 372 is not lysine, the amino acid at a position 503 is not alanine or valine, the amino acid at a position 511 is not isoleucine or lysine, the amino acid at a position 544 is not alanine or arginine, and the amino acid at a position 550 is not methionine or threonine, wherein the positions correspond to positions of SEQ ID NO:2.

In other embodiments, the composition includes (a) an amino acid sequence that has at least 95% sequence identity with SEQ ID NO:2; and (b) at least one, two, three, four, five, six or all seven of the following amino acid substitutions selected from the group consisting of: a lysine that replaces alanine at position 147, a tyrosine that replaces arginine at position 221, a glycine that replaces alanine at position 318, methionine that replaces alanine at position 503, valine that replaces isoleucine at position 511, lysine that replaces an arginine at position 544, and lysine that replaces threonine at position 550. Additional substitutions may occur at any or all of positions 339, 359, 383 and 384. Alternatively, the composition has at least 99% sequence identity with SEQ ID NO:5. In these embodiments, the composition has one or more improved DNA polymerase properties relative to wild-type Phi29 DNA polymerase tested under the same experimental conditions. The improved properties may include one or more of: an increased thermostability, for example at temperatures of 30° C.-45° C.; an increased reaction rate for DNA amplification over a defined period (e.g. 120 minutes or less), wherein the increase is at least 10%; a greater yield of amplified DNA; a reduction in background amplification arising from artefacts (nonspecific amplification in the absence of template); a reduction of bias that causes under-representation of GC rich regions and over-representation of AT rich regions; and a reduction in undesirable chimeric amplicons such as formed from primer-template fusions, non-sequential template sequences, or primer-non-sequential template sequences.

In any of the embodiments described above, the composition may be a fusion protein. The composition may be in a mixture of the variants with other types of polymerases and/or other enzymes with different substrate specificities.

In another aspect, the composition may include a buffering agent and may further include: dNTPs and/or modified dNTPs and/or one or more primers.

In one embodiment, a kit is provided that contains: (i) a DNA polymerase of the type described above; and (ii) a buffer. The kit may contain the DNA polymerase in a lyophilized form or in a storage buffer and/or with the reaction buffer in concentrated form. The kit may contain the DNA polymerase in a mastermix suitable for receiving template nucleic acid for causing amplification to occur. The DNA polymerase may be a purified enzyme so as to contain substantially no DNA or RNA and no nucleases. The reaction buffer in (ii) and/or storage buffers containing the DNA polymerase in (i) may include non-ionic, ionic e.g. anionic or zwitterionic surfactants and crowding agents. The kit may additionally contain one or more primers such as for example, random primers, exonuclease-resistant primers or primers having chemical modifications. The kit may further include one or more dNTPs including those dNTPs with large adducts such as a fluorescent-label or biotin-modified nucleotide, or a methylated nucleotide or other modified nucleotide. The kit may include the DNA polymerase and reaction buffer in a single tube or in different tubes.

In one aspect, a DNA encoding a DNA polymerase such as described above is provided. In another aspect, a host cell containing DNA for encoding the above described DNA polymerase is provided.

In general, a method for isothermal amplification of a target DNA is provided that includes combining the target DNA with a DNA polymerase of the type described above, dNTPs or modifications thereof and, optionally, one or more primers, to produce a reaction mixture; and incubating the reaction mixture to amplify the target DNA. The amplification reaction may be performed at a temperature in the range of 30° C.-42° C. and optionally a high salt buffer. The target DNA may be a whole genome or a target DNA sequence therein. The target DNA may be linear or circular.

In one aspect, the isothermal amplification of the target DNA is achieved using a DNA polymerase variant that includes for example (1) (a) an amino acid sequence having at least 95% sequence identity with SEQ ID NO:2; and (b) at least one, two, three, four, five, six or all seven of the following amino acid substitutions selected from the group consisting of: a lysine that replaces alanine at position 147, a tyrosine that replaces arginine at position 221, a glycine that replaces alanine at position 318, methionine that replaces alanine at position 503, valine that replaces isoleucine at position 511, lysine that replaces an arginine at position 544, and lysine that replaces threonine at position 550. Additional substitutions may occur at any or all of positions 339, 359, 383 and 384; or (2) at least 99% sequence identity with SEQ ID NO:5. Using the same molar ratio of polymerase to substrate where the target DNA is either linear or circular, one or more improved properties relative to wild-type Phi29 DNA polymerase was achieved. The improved properties include one or more of the following: an increased thermostability; an increased reaction rate for DNA amplification, wherein the increase may be at least 10%; increased yield of amplified DNA; reducing background amplification arising from artefacts; and reduced bias against GC rich regions and in favor of AT rich regions, to provide an even coverage of the substrate DNA.

BRIEF DESCRIPTION OF THE DRAWINGS

The skilled artisan will understand that the drawings, described below, are for illustration purposes only. The drawings are not intended to limit the scope of the present teachings in any way.

FIG. 1A shows that the variant DNA polymerase is not only capable of RCA at 37.6° C. and 42° C. as well as at 30° C. but it actually performs significantly better at the higher temperatures producing yields (indicated by the RFU on the y-axis, reflective of the amount of DNA produced in the reaction) that are close to maximum at 60 minutes. Moreover, the yields are significantly higher than observed for the wild-type Phi29 DNA polymerase used as a control.

FIG. 1B shows that wild-type Phi29 polymerase is active here only up to 30° C. and not at the higher temperatures tested. Moreover, yields from this reaction did not approach their maximum until at least 220 minutes of incubation.

FIG. 1C shows that the variant DNA polymerase is not only capable of WGA at 37.3° C. and 41.5° C. as well as at 30° C. and produced higher yields of products at the higher temperatures. For example, the time taken for the variant DNA polymerase to produce a yield of 4000 RFU at 41.5° C. was 26 minutes. The time taken for the mutant to produce the same amount of product at 37.5° C. was 27 minutes, whereas at 30° C. the time taken was 58 minutes.

FIG. 1D shows that the wild-type Phi29 polymerase control was not active at 37.3° C. nor at 41.5° C., and at 30° C. it took 87 minutes to reach 4000 RFU. The maximum yield was similar to the variant DNA polymerase at 30° C.

FIG. 2A shows that the variant DNA polymerase produces a high yield of amplified DNA at all temperatures tested: 30° C., 30.7° C., 32.3° C., 34.6° C., 37.6° C., 39.9° C., 41.3° C. and 42° C. However, yields increased significantly at 34.6° C., 37.6° C., 39.9° C., 41.3° C. and 42° C.

FIG. 2B shows that the wild-type Phi29 polymerase control only produced amplified DNA at 30° C., 30.7° C., 32.3° C., 34.6° C. with an end point yield comparable to the variant DNA polymerase at low temperatures, after which no product was detected.

FIG. 3A shows the increase in yield of DNA (ng/µl) using WGA with the variant DNA polymerase at all temperatures tested.

FIG. 3B shows the yield of DNA (ng/µl) using WGA with the control wild-type Phi29 DNA polymerase at the same temperatures as FIG. 3A where the yield is significantly less at 30° C.

FIG. 3C shows the results of qPCR analysis of amplified target over total DNA (1 ng Hela genomic DNA) showing that the variant DNA polymerase (at 41.5° C.) generated a higher fraction of the target DNA with less undesirable background amplification of primer sequences compared with the control Phi29 polymerase (at 30° C.). The amount and evenness of specifically amplified DNA (as opposed to non-specific amplification products and biased amplification) in the amplified product was determined by qPCR using 4 pairs of primers for target DNA sequences located on different chromosomes (3p, 4p, 7p and 13p). The amount of specifically amplified DNA was calculated as a fraction of the total DNA quantified by PicoGreen® (Molecular Probes, Eugene, Oreg.).

FIG. 3D shows that total yield of amplified DNA using the variant DNA polymerase is 5000-fold and with the wild-type is 3500-fold when detected using PicoGreen, under the conditions used in FIG. 3C with 1 ng input genomic DNA (gDNA) for amplification.

The solid line (circles) shows reactions using 1 ng of DNA template (Hela DNA) and variant DNA polymerase. The dotted line (triangles) is an identical reaction with primers but lacking DNA template (NTC).

DNA was quantified using PicoGreen in this experiment.

Figure 5:
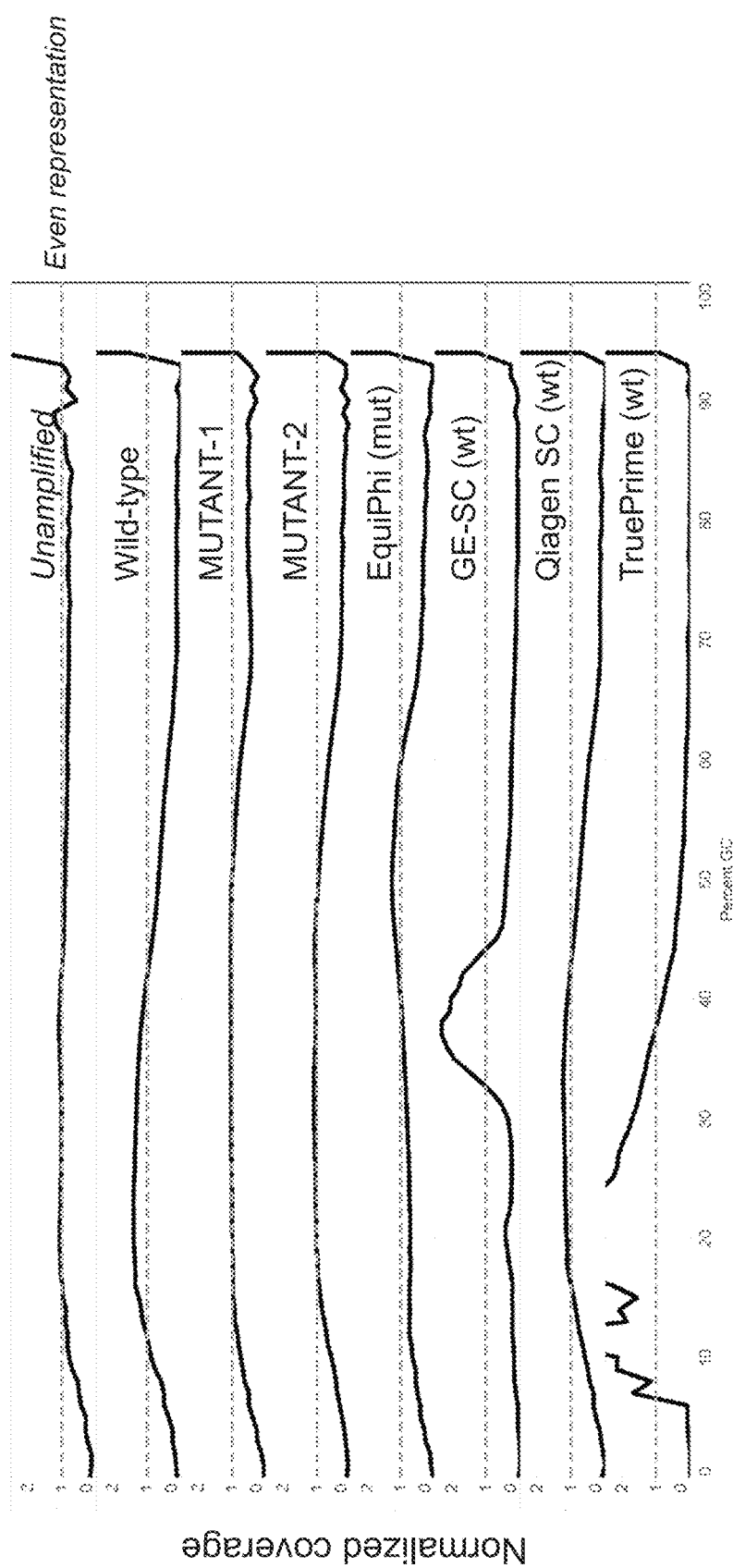

FIG. 5 shows the mutant polymerase produces amplified DNA that represents even coverage of gDNA template as measured via DNA sequencing. Examples of the mutants used here are Mutant 1 (SEQ ID NO:5) and Mutant 2 (SEQ ID NO:6)

FIG. 6 shows an alignment of selected wild-type and mutant polymerases that share the properties of the polymerases described herein.

DETAILED DESCRIPTION OF THE EMBODIMENTS

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference. Preferably, any further interpretations of terms should be consistent with U.S. Pat. No. 10,034,951.

As used herein, the term "DNA polymerase" refers to an enzyme that is capable of replicating DNA. The enzyme may also have reverse transcriptase properties. Examples of polymerases from the phage Phi29 family include polymerases from phages Phi29, B103, GA-1, PZA, Phi15, BS32, M2(Y) and Nf (Microbiology and Molecular Biology Reviews, 65(2), 261-286 (2001)).

As used herein, the term "DNA polymerase variant" and "DNA polymerase mutant" refers to a non-naturally occurring bacteriophage DNA polymerase that has an amino acid sequence less than 100% identical to the amino acid sequence of a wild-type DNA polymerase from Phi29 family of phages. A variant amino acid sequence may have at least 80%, at least 85%, at least 90%, at least 95%, at least 97%, at least 98% or at least 99% identity to the naturally occurring amino acid sequence. Sequence differences may include insertions, deletions and amino acid substitutions.

A mutant or variant protein may be a "fusion" protein. The term "fusion protein" refers to a protein composed of a plurality of polypeptide components that are un-joined in their native state. Fusion proteins may be a combination of two, three or even four or more different proteins. The term polypeptide is not intended to be limited to a fusion of two heterologous amino acid sequences. A fusion protein may have one or more heterologous domains added to the N-terminus, C-terminus, and or the middle portion of the protein. If two parts of a fusion protein are "heterologous", they are not part of the same protein in its natural state.

Examples of fusion proteins includes a Phi29 variant fused to an SSO7 DNA binding peptide (see for example, U.S. Pat. No. 6,627,424), a transcription factor (see for example, U.S. Pat. No. 10,041,051), a binding protein suitable for immobilization such as maltose binding domain (MBP), chitin binding domain (CBD) or SNAP-Tag® (New England Biolabs, Ipswich, Mass. (see for example U.S. Pat. Nos. 7,939,284 and 7,888,090). The binding peptide may be used to improve solubility or yield of the polymerase variant during the production of the protein reagent. Other examples of fusion proteins include a heterologous targeting sequence, a linker, an epitope tag, a detectable fusion partner, such as a fluorescent protein, β-galactosidase, luciferase and the functionally similar peptides.

As used herein, the term "buffering agent", refers to an agent that allows a solution to resist changes in pH when acid or alkali is added to the solution. Examples of suitable non-naturally occurring buffering agents that may be used in the compositions, kits, and methods of the invention include, for example, any of Tris, HEPES, TAPS, MOPS, tricine, and MES.

The buffering agent which may be combined with the polymerase variant, may further include additional reagents such as crowding agents (such as polyethylene glycol included in the storage and/or reaction mixture), single strand binding proteins or portions thereof, unwinding agents such as helicases, detergents such as nonionic, cationic, anionic or zwitterionic detergents, additives such as albumin, glycerol, salt (e.g. KCl), reducing agent, EDTA, dyes, a reaction enhancer or inhibitor, an oxidizing agent, a reducing agent, a solvent and/or a preservative. The buffering agent combined with additional reagents that are standard in the art may be formulated for storage of the Phi29 variant or for the reaction mixture. The formulation for storage of the polymerase variant or for an amplification reaction may be the same or different.

The polymerase may be prepared for storage as a reagent or contained in a mastermix for storage. Alternatively, the polymerase may be contained in a reaction buffer or mastermix. The reaction mix and the storage mix may be the same or different. The storage mix may be a concentrated form of the reagent for dilution into a reaction mix. In one example, the polymerase variant may be in a lyophilized form. In another example, the polymerase variant may be in a master mix containing deoxyribose nucleoside triphosphates e.g. one, two, three or all four of dATP, dTTP, dGTP and dCTP and/or one or more modified dNTPs. The composition may optionally comprise primers. In some embodiments, the primers may be partially or complete random. In some embodiments, the primers may be exonuclease-resistant. In some embodiments, primers may comprise one or more chemical modifications, for example, phosphorothioate modifications. In some embodiments, the chemical modifications on the primers may occur at 3'-terminal or both of 3' and 5' terminals of the primers. In some embodiments, the chemical modifications on the primers may further occur at one or more non-terminal positions of the primers.

The term "non-naturally occurring" refers to a composition that does not exist in nature. A "non-naturally occurring" protein may have an amino acid sequence that is different from a naturally occurring amino acid sequence for example, one or more amino acid substitutions, deletions or insertions at the N-terminus, the C-terminus and/or between the N- and C-termini of the protein. Hence the non-naturally occurring protein may have less than 100% sequence identity to the amino acid sequence of a naturally occurring protein although it may have least 80%, at least 85%, at least 90%, at least 95%, at least 97%, at least 98%, at least 98.5% or at least 99% identical to the naturally occurring amino acid sequence. In certain cases, a non-naturally occurring protein may include a protein that has a post-translational modification pattern that is different from the protein in its natural state for example, an N-terminal methionine or may lack one or more post-translational modifications (e.g., glycosylation, phosphorylation, etc.) if it is produced by a different (e.g., bacterial) cell.

In the context of a nucleic acid, the term "non-naturally occurring" refers to a nucleic acid that contains: a) a sequence of nucleotides that is different from a nucleic acid in its natural state (i.e., having less than 100% sequence identity to a naturally occurring nucleic acid sequence); b) one or more non-naturally occurring nucleotide monomers (which may result in a non-natural backbone or sugar that is not G, A, T or C); and/or c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

The non-naturally occurring polymerase may be purified so that it does not contain DNases, RNases or other proteins with undesirable enzyme activity or undesirable small molecules that could adversely affect the sample substrate or reaction kinetics.

The term "corresponding to" in the context of corresponding positions, refers to positions that lie across from one another when sequences are aligned, e.g., by the BLAST algorithm.

DNA Polymerase Variants and Compositions Containing the Same

Provided herein is a Phi29 like DNA polymerase identified as bacteriophage B103 DNA polymerase (SEQ ID NO:2), M2(Y) DNA polymerase (SEQ ID NO:3) and Nf DNA polymerase (SEQ ID NO:4). Non-natural variants of B103 are described by SEQ ID NOs:5-27.

The examples demonstrate the assay for and detection of improved properties using one of the variants (SEQ ID NO:5). In some embodiments, the variant has an amino acid sequence that has at least 98%, at least 98.5% or at least 99% identical to SEQ ID NO:2. For example, the variant may have one or more (e.g., one, two, three, four, five or more than five) amino acid substitutions at positions from the group consisting of 73, 147, 221, 318, 503, 511, 544, 550. Examples of one or more, two or more, three of more, four or more, five or more, six or more or seven or more mutations at these sites include: H73R, A147K, R221Y, A318G, A503M, I511V, R544K, T550K. Additionally, one or more substitutions may be selected from position 339, 359, 372, 383 and 384. Alternatively, when a variant has a mutation at position 339, 359, 372, 383 and/or 384, it also has at least one mutation selected from: H73R, A147K, R221Y, A318G, A503M, I511V, R544K, and T550K. In some embodiments, the variant may have an amino acid sequence that is at least 98.5%, at least 99% or 100% identity to the amino acid sequence of SEQ ID NO:5.

In some embodiments, the variant DNA polymerase may have an amino acid sequence that is at least 80%, or at least 90% identical to SEQ ID NO:1 (i.e., the wild-type Phi29 DNA polymerase). In some embodiments, the variant DNA polymerase may have one or more substitutions at positions selected from the group consisting of: V16, E17, N28, E30, D31, H32, S33, E34, A46, L49, K50, 168, N74, A80, D81, R93, L104, I112, T137, V138, Y153, K154, A161, Q168, E172, L175, I199, T200, K205, T210, G214, V219, R233, F234, L259, E264, E269, V273, W274, D277, H284, C287, R303, S304, R305, Y307, S315, I320, A321, D322, W324, S326, M333, K334, D338, S346, L348, K351, A352, T353, I367, T370, S371, N406, A408, L413, E415, T418, Y436, I464, D466, V467, G513, D517, Y518, D520, I521, K533, E537, E541, R549, M551, P559, D567, T568 corresponding to positions of SEQ ID NO:1.

In some embodiments, the DNA polymerase variant may comprise an amino acid sequence that is at least 80% or at least 90% identical to SEQ ID NO:1, it may further comprise one or more amino acid substitution selected from the group consisting of: V16L, E17D, N28E, E30G, D31N, H32L, S33D, E34N, A46Q, L49M, K50E, 168V, N74H, A80N, D81E, R93K, L104F, I112L, T137P, V138L, Y153H, K154E, A161E, Q168E, E172R, L175D, I199L, T200S, K205N, T210K, G214P, V219I, R233K, F234Y, L259P, E264A, E269Q, V273E, W274K, D277Q, H284R, C287F, R303K, S304N, R305P, Y307F, S315N, I320P, A321V, D322E, W324Y, S326T, M3331, K334Q, D338E, S346D, L348F, K351R, A352E, T353K, I367V, T370H, S371E, N406D, A408S, L413V, E415D, T418Y, Y436F, I464V, D466E, V467I, G513C, D517E, Y518A, D520T, I521T, K533T, E537K, E541D, R549S, M551G, P559N, D567S, T568V corresponding to positions of SEQ ID NO:1.

In some embodiments, the DNA polymerase variant may have an amino acid sequence that is at least 95% identical to SEQ ID NO:3 (the wild-type M2(Y) DNA polymerase) and may further comprise at least one substitution at positions corresponding to SEQ ID NO:3, wherein the position is selected from the group consisting of: S2, Q73, T147, K221, V318, V503, K511, A544, M550. These substitutions may further comprise: S2P, Q73R, T147K, K221Y, V318G, V503M, K511V, A544K, and/or M550K. In one embodiment, the variant may optionally lack any mutations at positions 359, 372, 383 and 384.

In some embodiments, the DNA polymerase variant may have an amino acid sequence that is at least 95% identical to SEQ ID NO:4 (wild-type Nf DNA polymerase) and may further comprise at least one substitution at positions corresponding to SEQ ID NO:4, wherein the position is selected from the group consisting of: S2, Q73, R107, T147, K221, V318, V503, K511, A544, M550. These substitutions may further comprise: S2P, Q73R, T147K, K221Y, V318G, V503M, K511V, A544K, and/or M550K. In one embodiment, the variant may optionally lack any mutations at positions 359, 372, 383 and 384.

Examples of reaction conditions are provided in the examples and figures. Providing incubation of the amplification reaction is permitted to occur for an extend period of time (e.g. 4 hours), the yield of amplified DNA reaches a plateau regardless of whether the DNA polymerase is a Phi29 family variant or wild type. However, with the variants, the rate of reaction is more rapid resulting in shorter incubation times to reach approximately maximum yield. The thermostability of the variant may contribute to the reduction of bias that occurs from high or low GC content. Hence the variant polymerase are more efficient at amplifying template DNA than the wild type phi29 under the same conditions.

The DNA polymerase variants described herein show improved properties compared to wild-type Phi29 DNA polymerase under the same conditions as exemplified by Mutant 1. Suitable variants preferably have increased polymerase activity at a temperature range of 30° C. to 45° C. relative to a wild-type Phi29 DNA polymerase and increased thermostability at least within a temperature range of 35° C.-42° C. Examples of suitable temperature ranges for the variants may include for example, 35° C. to 40° C., 40° C. to 45° C. or 35° C. to 50° C.

DNA polymerase variants described herein showed the improved properties of thermostability, reduction in template independent products, increased overall yield of amplified product, and higher amplification efficiency, Increased thermostability of the variants at elevated temperature provides an increase in amplification product with reduction in DNA sequence bias as a measure of the efficiency of the reaction over a selected time period (e.g. 100 minutes or 120 minutes). The increase in yield of amplification product for exemplified time periods may be at least 10% more, at least 20% more, at least 50% more, at least 100% more, at least 200% or at least 250% compared with the wild-type Phi29 DNA polymerase under the same conditions.

The significant increases in yield achieved with the variants is shown in FIGS. 1A-1D, 2A-2B and 3A-3D where the thermostability of selected variants (e.g. Mutant 1) at elevated temperatures permits a significant increase in the yield of amplification products of target DNA during a selected time period of the reaction (for example, within the first 120 minutes) where the yield at 41.5° C. and 37.5° C. was compared to 30° C. using either RCA or WGA amplification methods. Similar results are expected for other isothermal amplification methods amenable to the use of the Phi29 family of polymerases.

Figure 3B:
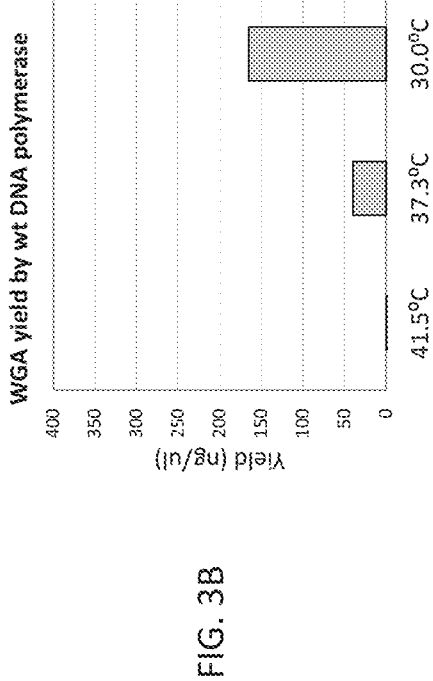
FIG. 3A-3D shows that use of the variant DNA polymerase increases the yield of amplification product in WGA and reduces background amplification at temperatures above 30° C. compared with the control Phi29 DNA polymerase.
Figure 3D:
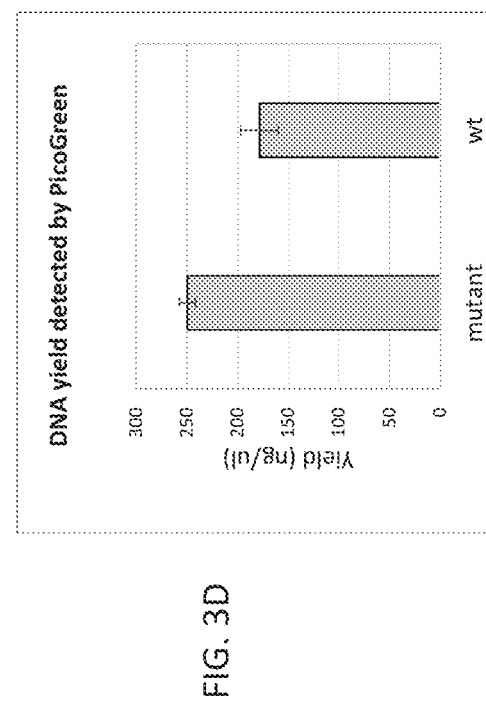
Figure 3A:
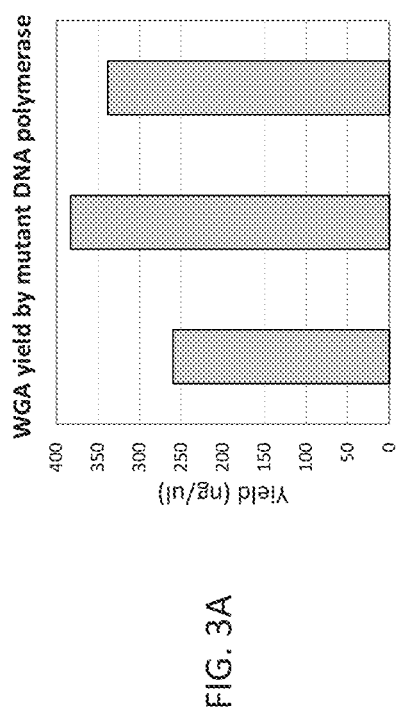
Figure 3C:
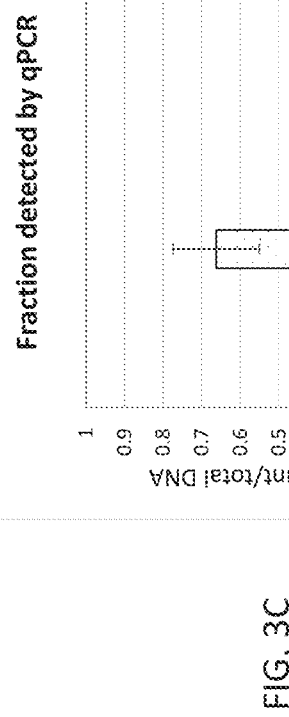

FIG. 3C and FIG. 5 and the Tables 1-4 provided evidence that the variants could reduce amplification bias against high and low GC regions and reduce chimera formation in amplified DNA. The use of the DNA polymerase variants at an elevated temperature reduced the background resulting from generation of undesired template-independent DNA in an amplification reaction to a negligible level. Taken together, the results show that at least those polymerase variants that have at least 98.5% or 99% sequence identity to SEQ ID NO:5 or at least 95% sequence identity with SEQ ID NO:2 with at least one, two, three, four, five, six or all amino acid substitution selected from the group consisting of: A147K, R221Y, A318G, A503M, I511V, R544K and T550K have both an improved rate of reaction leading to at least the same or higher maximum yield of product DNA with less bias against high GC or low GC template DNA. This combination is referred to as the improved efficiency of amplification with the variants. An additional benefit of the use of these variant polymerases is the significant reduction to negligible levels on non-template amplification (see FIG. 4).

The DNA variants described herein show reduced bias in amplification of substrate DNA so that WGA of a genome provided an even and unbiased amplification of all regions of varying GC content as determined by sequencing that was sequence platform independent (see for example, FIG. 5).

For example, Table 1 shows that the DNA polymerase variant has an improved ability to evenly amplify mixed genomic DNAs of varying GC content including *Rhodopseudomonas palustris* (65% GC content) and *Haemophilus influenzae* (38% GC). Formulations of wild-type Phi29 produced very few sequencing reads from *R. palustris* genome while a high percentage of the total reads were represented by the *H. influenzae* genome. In contrast, the variants described herein produced sequencing reads from the high GC gDNA that matched the mixed pool demonstrating more even and less biased amplification of the mixed pool. Table 2 shows that the DNA polymerase variant produced significantly fewer chimeric sequencing reads in a long-read nanopore sequencing experiment than did the wild-type Phi29 where the chimera may be formed by amplification of target DNA or in a non-sequential manner due to annealing and folding of the target genomic DNA.

In embodiments, a method is provided for isothermal amplification of target DNA using a DNA polymerase variant as described herein. Accordingly, the target DNA is combined with the variant DNA polymerase and dNTPs to produce a reaction mixture preferably further including one or more primers; and the reaction mixture incubated to amplify the target DNA.

Accordingly, the DNA polymerase variants were demonstrated to provide improved results with strand displacement amplification, RCA and MDA. For example, the DNA polymerase variants were used in conjunction with random primers to amplify circularized DNA by RCA to produce high yields of product (for an explanation of RCA see, e.g., Dean et al., Genome Res. 11: 1095-1099 (2001)). For RCA, oligonucleotide primers that are complementary to the target circle of DNA hybridize to the sample. The addition of DNA polymerase and deoxynucleoside triphosphates (dNTPs) to the primed circle result in the extension of each primer. Displacement of the newly synthesized strands result from elongation of the primer behind it. Secondary priming events can subsequently occur on the displaced product strands of the initial RCA step.

The mutant may also be used in other quantitative amplification methods in the art.

Kits are described herein that include a DNA polymerase variant as described herein. Additional polymerases and other enzymes may be included in the kit. The DNA polymerase may be in a storage buffer (which may contain glycerol). A reaction buffer may be included which may be in concentrated form, and the buffer may contain additives (e.g. glycerol), salt (e.g. KCl), reducing agent, EDTA or detergents, etc. The kit may further comprise deoxyribose nucleoside triphosphates e.g. one, two, three of all four of dATP, dTTP, dGTP and dCTP and/or one or more modified nucleotides. The kit may optionally comprise one or more primers. The components of the kit may be combined in one container for a single step reaction, or one or more components may be contained in one container and separated from other components for sequential use or parallel use. The kit may also contain other reagents described above that may be employed in the method depending on how the method is going to be implemented.

All publications, patents, and patent applications mentioned in this specification are herein incorporated by reference to the same extent as if each individual publication, patent, or patent application was specifically and individually indicated to be incorporated by reference including U.S. Provisional Application No. 62/743,718 filed Oct. 10, 2018.

EXAMPLES

Example 1: Multiply Primed Rolling Circle Amplification (MP-RCA)

Figure 1A:
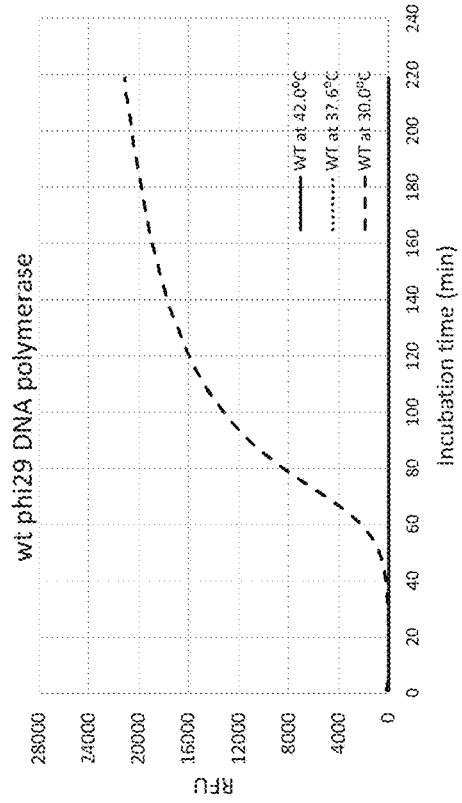
FIG. 1A-1D shows that a variant of the B103 DNA polymerase (referred to as "mutant" in the figures) that has the amino acid sequence of SEQ ID NO:5 generates amplification products by RCA and WGA with higher yield (RFU) and in a shorter time than wild-type Phi29 polymerase at all temperatures tested. As shown here, wild-type Phi29 is not active above 30° C., whereas the variant is active at 42° C.
Figure 1B:
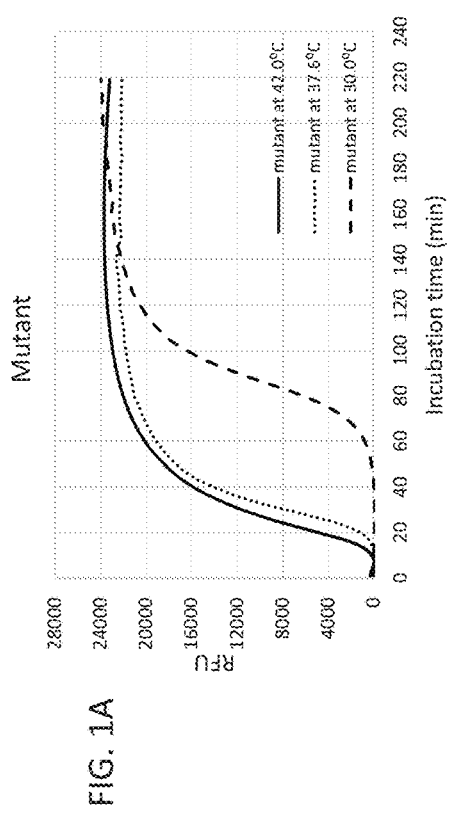
Figure 1C:
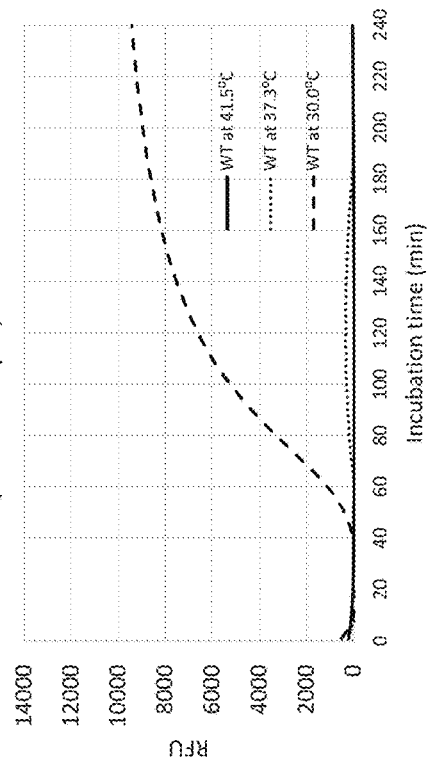
Figure 1D:
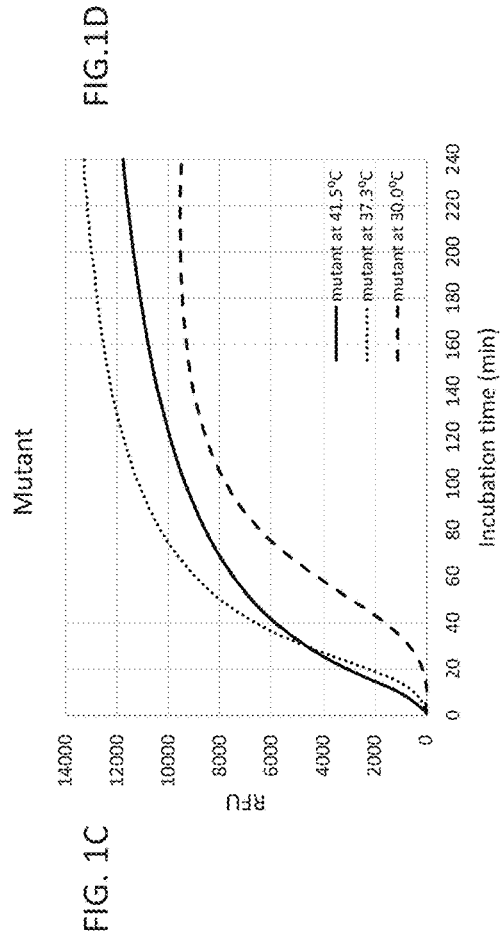

Wild-type Phi29 DNA polymerase has been extensively used in multiply primed rolling circle amplification (MP-RCA) reaction under a low reaction temperatures such as 30° C.-34° C. (de Vega, et al., PNAS, 107, 38:16506-16511 (2010); Dean, et al., Genome Research, 11, 6:1095-1099 (2001)). To characterize the thermostability of the bacteriophage DNA polymerase mutant, MP-RCA was performed at different temperatures and compared with wild-type Phi29 polymerase. 50 µM of random 6 base primer that contained two phosphorothioate linkages at the 3' end and 1 ng of pUC19 template were first annealed by heating to 95° C. for 3 minutes in a buffer (37 mM Tris, 50 mM KCl, 5 mM $(NH_4)_2SO_4$, 10 mM $MgCl2$, 0.025% Tween 20, pH 7.5) and subsequently cooled down to room temperature. Equivalent amounts of either wild-type or mutant polymerase was added into the reaction mixture and incubated at various times up to 4 hours at different reaction temperatures ranging from 30° C. to 42° C. The reaction mixture was then heated for 10 minutes at 65° C. to inactivate the polymerases. The real-time monitoring of the MP-RCA reaction was performed by adding 1 µM of double stranded DNA binding dye SYTO®9 (Molecular Probes, Eugene, Oreg.)) into the reaction mixture. The fluorescence of the dye was detected using a CFX96 Touch™ Real-Time PCR detection system (Bio-Rad, Hercules, Calif.) (FIG. 1A-1B). The amplification product was then cleaved into fragments by HindIII restriction endonuclease (New England Biolabs, Ipswich, Mass.) and analyzed in TBE agarose gel (FIG. 2A-2B).

Figures 2A, 2B:
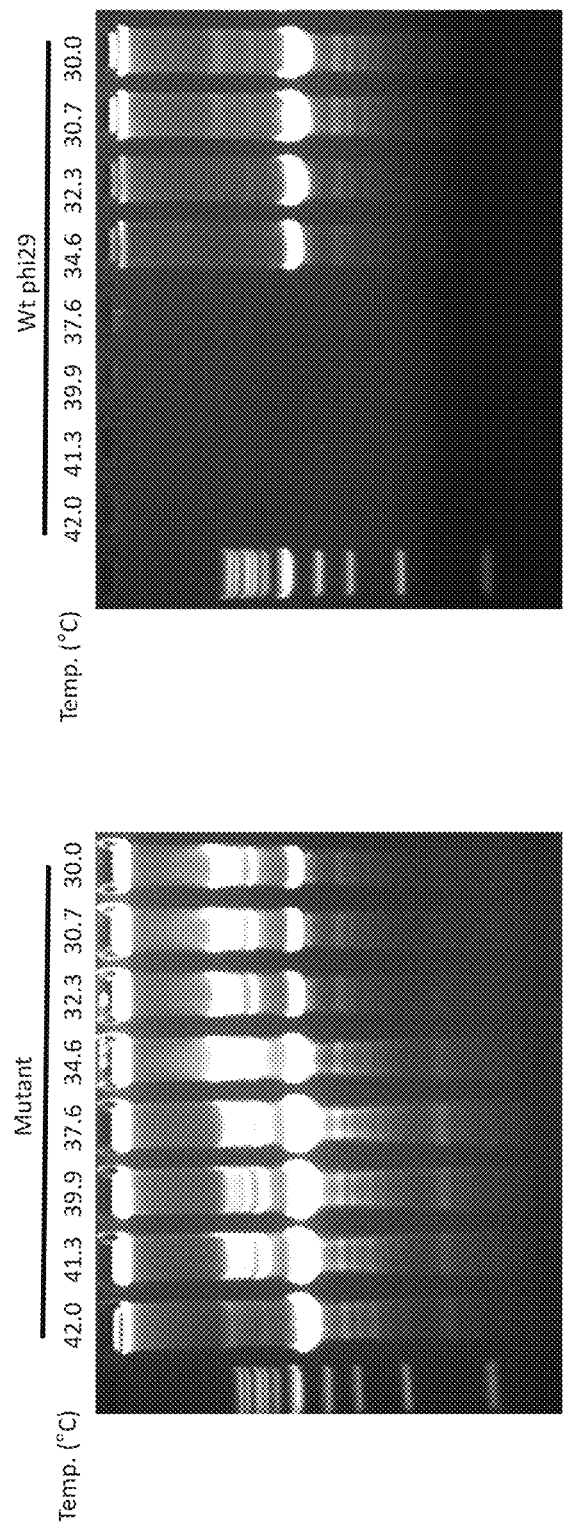
FIG. 2A-2B shows that variant DNA polymerase provides an increased yield of RCA amplification product at temperatures above 32° C. up to and including 42° C. compared with the wild-type Phi29 DNA polymerase.

The DNA polymerase mutant generated more amplification products under a broad range of reaction temperature (e.g. 30° C.-42° C.) as relative to wild-type Phi29 polymerase (FIG. 2A, FIG. 2B). While the polymerase activity of the wild-type significantly decreased when the reaction temperature was above 37° C., it was unexpected to find the mutant showed increased reaction rate for DNA amplification when the reaction temperature elevated.

As shown in FIG. 2A-2B, for example, the reaction rate was at least 15-fold higher during the first 50 minutes of the reaction at elevated temperatures (e.g. 37.6° C. and 42.0° C.) than the otherwise identical reaction at a lower temperature (e.g. 30° C.).

Example 2: Whole Genome Amplification (WGA)

WGA reaction was performed using 1 ng genomic DNA from HeLa cells as template. The reaction condition was otherwise identical to MP-RCA as described above.

The real-time monitoring of the WGA reaction (FIG. 1C-1D) showed a higher amplification efficiency when using the bacteriophage DNA polymerase mutant over a broad range of reaction temperatures (e.g. 30° C. to 41.5° C.). For example, during the first 50 minutes of the WGA reaction at 30° C., the mutant generated at least 1-fold more amplification product as relative to wild-type Phi29 polymerase, which further increased to over 2-fold at 37.3° C. At a temperature of 41.5° C., the wild-type Phi29 polymerase had completely lost any detectable enzymatic activity, while the mutant still showed high efficiency of amplification.

As shown in FIG. 3A-3B, the bacteriophage DNA polymerase mutant generated at least 2-fold more amplification products as relative to wild-type Phi29 polymerase after a 4-hour incubation which time frame was selected as the plateau of amplification yield as illustrated in FIG. 1A-1D. The yield increase was even more significant with the temperature elevation, for example, to at least 9-fold above 35° C. In contrast, the amplification yield when using wild-type Phi29 polymerase decreased over four-fold when the temperature was elevated from 30° C. to 37.3° C., and there was no amplification product generated at 41.5° C.

Evenness of amplification is shown in FIG. 3C where the quantity of specific DNA sequences was measured with quantitative PCR at 4 distinct chromosomal locations (3p, 4p, 7p, 13p). The quantity of the DNA from each loci was compared to an unamplified control DNA standard and normalized for the amount of amplified DNA product (FIG. 3D). A value of 1 (y-axis) indicates perfectly even amplification and 0 a failure to amplify. As shown the mutant enzyme produced DNA closer to even amplification at all 4 loci, whereas products from wild-type phi29 showed very low amplification of the specified regions despite production of significant quantities of DNA. The wild-type products therefore represent less-even amplification and/or production of nonspecific, template-independent DNA.

Figure 4:
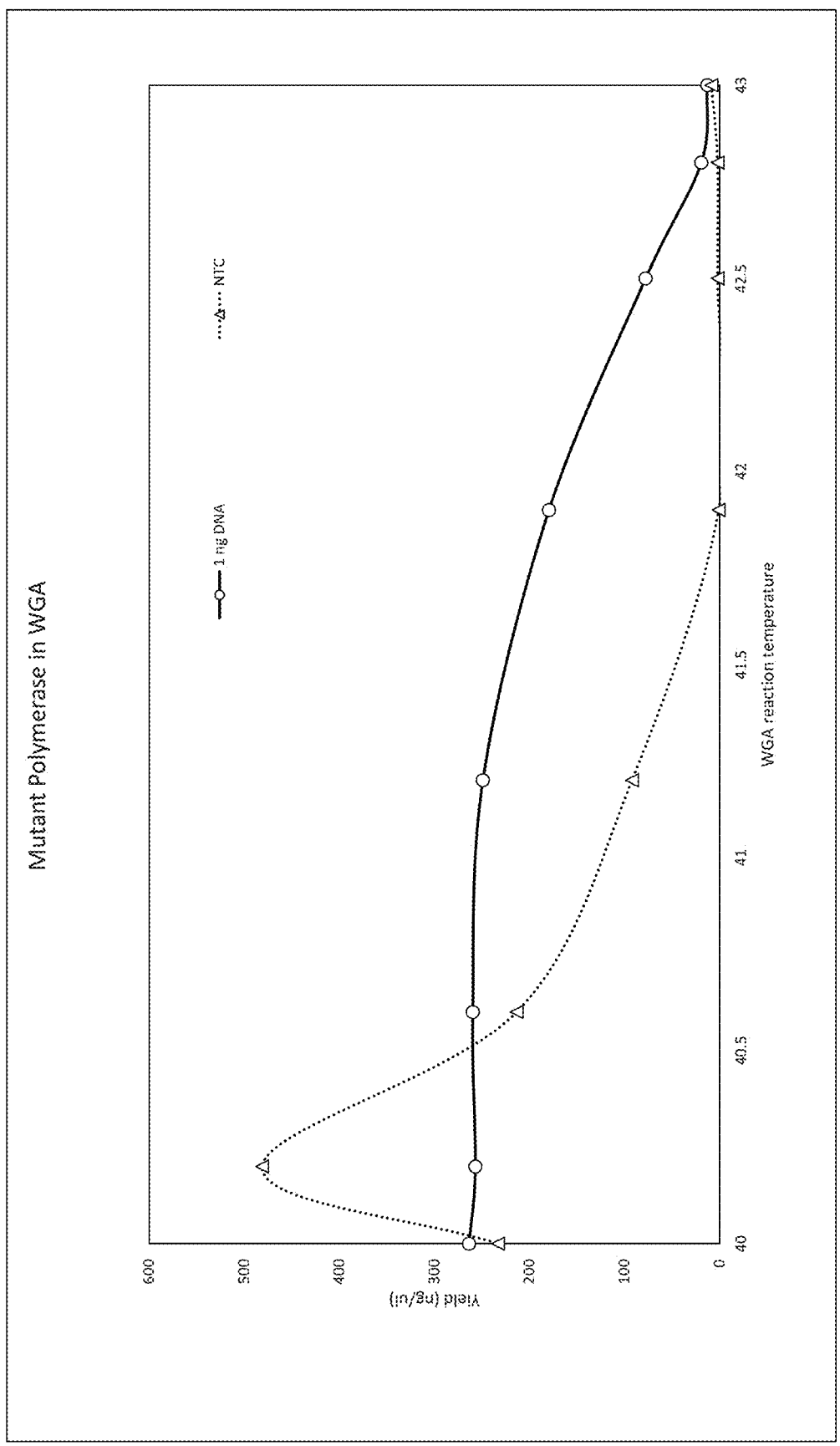
FIG. 4 shows that WGA with the mutant polymerase can be conducted at elevated temperature (to 42° C.) with high yield of amplification product and reduction of non-specific amplification. The no template control (NTC) reaction produces high yield of DNA product at lower temperatures, but at temperatures of greater than 41° C. the NTC reaction is substantially suppressed while the positive reaction continues to produce high yield.

The template-independent DNA amplification was assessed by performing the otherwise identical reaction in the absence of template gDNA and measuring the product generated by nonspecific primer-directed DNA synthesis (FIG. 4). The accumulation of these template-independent products may severely decrease the specificity of WGA reaction. The ability of the mutant polymerase to perform WGA at elevated (42° C.) temperature not only facilitates higher yield and more even coverage as described but reduces the level on nonspecific amplification (FIG. 4) with random hexamer primers in conditions above.

Example 3: Next-Generation Sequencing (NGS) Analysis Using Illumina Sequencing

DNA of 3 genomes (R. palustris, E. coli, H. influenzae) varying in GC content was mixed and used as template for WGA. The WGA was performed at 41.5° C. (mutant) for 4 hours or as recommended by the commercial WGA formulations including wild-type (Illustra® Single-Cell GenomiPhi DNA Amplification Kit (GE Healthcare, Life Sciences, Marlborough, Mass.), REPLI-g® Single Cell Kit (Qiagen, Germantown, Md.) TruePrime® (Expedeon, San Diego, Calif.)) or different mutant (EquiPhi™ Phi29 (ThermoFisher Scientific, Waltham, Mass.)) phi29 DNA polymerases. Reactions contained 100 pg input of the mixed genomic template DNA and incubated for 2 hours or as recommended. The WGA product was then purified and prepared for Illumina NextSeq® sequencing (Illumina, San Diego, Calif.) following standard protocol. Unamplified DNA was also sequenced as a control. The percentage of reads that mapped to each individual genome was calculated and normalized to the unamplified sample reads, where 1 equals an exact match to the unamplified sample, a value >1 indicates over-amplification and <1 under amplification.

These results are shown in Table 1 below and indicate a more equal amplification of all 3 genomes by the Mutant 1 DNA polymerase as compared to the alternative WGA formulations.

TABLE 1

Demonstration of improved even coverage of 3 amplified genomes compared to the alternative WGA formulations using commercial Phi29 polymerases using an Illumina NextSeq platform.

| WGA Polymerase | H. inf (38% GC) | E. Coli (50% GC) | R. Palustris (65% GC) |
| --- | --- | --- | --- |
| Unamplified | 1 | 1 | 1 |
| MUTANT 1 | 1.9 | 1.1 | 0.51 |
| Thermo EquiPhi (mut.) | 2.1 | 1.8 | 0.029 |
| GE-SC (wt) | 0.54 | 2.02 | 0.69 |
| True Prime (wt) | 4.1 | 0.00054 | 0.000051 |
| Qiagen SC (wt) | 3.2 | 0.84 | 0.0025 |

To analyze with complex (human genomic) DNA, Illumina sequencing reads using libraries prepared from WGA reactions using the indicated WGA polymerase and human gDNA show even coverage (FIG. 5). 100 ng of DNA from each reaction was converted to Illumina libraries using the NEBNext® Ultra™ II Kit (New England Biolabs, Ipswich, Mass.) with barcoded adaptors, and sequenced on a NextSeq instrument with reads down sampled to an equivalent number for each amplification method. The genome was separated into 100 bp regions and the GC percentage calculated for each, and the number of reads representing each region graphed relative to its natural frequency in the genome (FIG. 5); i.e. perfect coverage of every region results in a straight line at y=1 on the graph. As shown, an unamplified library made from pure genomic DNA (100 ng) results in the flattest profile, with using two examples of mutant polymerases described herein producing similarly even (flat) coverage. Commercial WGA formulations using wild-type Phi29 and recommended conditions (illustra Single-Cell GenomiPhi DNA Amplification Kit, REPLI-g Single Cell Kit, TruePrime) as well as a different mutant polymerase at elevated temperature (EquiPhi, 45° C.) produce more uneven coverage as seen with overamplified (>1) and underamplified (<1) regions.

Example 4: Analysis by Oxford Nanopore Sequencing

DNA of 4 genomes (*R. palustris, E. coli, H. influenza, P. falciparum*) varying in GC content was mixed at certain ratio and used as template for WGA. The WGA was performed with 100 pg input of the mixed genomic template DNA and incubated for 2 hours (wild-type, 30° C.; and mutant Phi29, 42° C.) or as instructed by manufacturer (Qiagen and GE). The WGA product was then prepared for Oxford Nanopore MinION sequencing (Oxford Nanopore Technologies, Oxford, UK) following standard protocols. The number of sequencing reads from each sample is shown in Table 2 below, with the number containing chimeric sequence (fusion of non-consecutive or opposite strand template sequence) and the percentage of chimeric reads out of the total indicated Table 2.

TABLE 2

| WGA Polymerase | Chimeric | Standard | % Chimeric |
| --- | --- | --- | --- |
| Qiagen SC (wt) | 45,943 | 68,315 | 40.2 |
| GE V3 (wt) | 142,873 | 219,883 | 39.4 |
| WT Phi29 | 39,430 | 43,290 | 47.7 |
| MUTANT 1 | 36,940 | 291,413 | 11.2 |

A similar analysis is shown in Table 3 wherein 100 pg of human (HeLa) genomic DNA was used as template for amplification. Mutant reaction was incubated for 2 hours at 42° C. or as recommended by the manufacturer. The percentage of reads containing chimeric DNA sequence is shown below and again indicates a reduced frequency of chimera formation with the mutant polymerase.

TABLE 3

| WGA Polymerase | Chimeric | Standard | % Chimeric |
| --- | --- | --- | --- |
| Unamplified | 194 | 39276 | 0.49% |
| MUTANT | 3,893 | 22,117 | 15% |
| Thermo EquiPhi (mut.) | 10,802 | 31,977 | 25% |
| GE-HY (wt) | 8,491 | 18,282 | 32% |
| True Prime (wt) | 5,223 | 23,065 | 18% |
| Qiagen SC (wt) | 7,053 | 18,610 | 27% |

These results show that the DNA polymerase variant at 42° C. produces significantly fewer chimeric DNA products as compared to wild-type Phi29 and standard WGA methods.

Example 5: Improved Error Rate of Mutant Phi29 Polymerase Using PacBio Sequencing DNA products were produced using a restriction enzyme-digested M13 DNA substrate using either wild-type or mutant Phi29 in a low salt (50 mM K-Acetate) or high salt (215 mM K-Acetate) buffer. DNA was prepared for Pacific Biosciences (Menlo Park, Calif.) RSII sequencing and the second strand error rate of the DNA polymerase calculated as described in (Potapov et, al., Nucleic Acids Res 46(11): 5753-5763 (2018)). In both buffer conditions the error rate of the Mutant Phi29 was ~2-fold lower versus the wild-type Phi29, showing that the reduction in error rate associated with the ability to perform reactions at 42° C. efficiently is a property of the DNA polymerase variant and not the buffer conditions.

TABLE 4

| Polymerase | Low salt error rate ($\times 10^{-6}$) | High salt error rate ($\times 10^{-6}$) |
| --- | --- | --- |
| Wild-type Phi29 | 15 | 17 |
| Mutant 1 | 9.2 | 8.6 |

SEQUENCE LISTING

SEQ ID NO: 1
MPRKMYSCDFETTTKVEDCRVWAYGYMNIEDHSEYKIGNSLDEFMAWVLK

VQADLYFHNLKFDGAFIINWLERNGFKWSADGLPNTYNTIISRMGQWYMI

DICLGYKGKRKIHTVIYDSLKKLPFPVKKIAKDFKLTVLKGDIDYHKERP

VGYKITPEEYAYIKNDIQIIAEALLIQFKQGLDRMTAGSDSLKGFKDIIT

TKKFKKVFPTLSLGLDKEVRYAYRGGFTWLNDRFKEKEIGEGMVFDVNSL

YPAQMYSRLLPYGEPIVFEGKYVWDEDYPLHIQHIRCEFELKEGYIPTIQ

IKRSRFYKGNEYLKSSGGEIADLWLSNVDLELMKEHYDLYNVEYISGLKF

KATTGLFKDFIDKWTYIKTTSEGAIKQLAKLMLNSLYGKFASNPDVTGKV

PYLKENGALGFRLGEEETKDPVYTPMGVFITAWARYTTITAAQACYDRII

YCDTDSIHLTGTEIPDVIKDIVDPKKLGYWAHESTFKRAKYLRQKTYIQD

IYMKEVDGKLVEGSPDDYTDIKFSVKCAGMTDKIKKEVTFENFKVGFSRK

MKPKPVQVPGGVVLVDDTFTIK

SEQ ID NO: 2
MPRKMFSCDFETTTKLDDCRVWAYGYMEIGNLDNYKIGNSLDEFMQWVME

IQADLYFHNLKFDGAFIVNWLEHHGFKWSNEGLPNTYNTIISKMGQWYMI

DICFGYKGKRKLHTVIYDSLKKLPFPVKKIAKDFQLPLLKGDIDYHAERP

VGHEITPEEYEYIKNDIEIIARALDIQFKQGLDRMTAGSDSLKGFKDILS

TKKFNKVFPKLSLPMDKEIRRAYRGGFTWLNDKYKEKEIGEGMVFDVNSL

YPSQMYSRPLPYGAPIVFQGKYEKDEQYPLYIQRIRFEFELKEGYIPTIQ

IKKNPFFKGNEYLKNSGAEPVELYLTNVDLELIQEHYEMYNVEYIDGFKF

REKTGLFKEFIDKWTYVKTHEKGAKKQLAKLMFDSLYGKFASNPDVTGKV

PYLKEDGSLGFRVGDEEYKDPVYTPMGVFITAWARFTTITAAQACYDRII

YCDTDSIHLTGTEVPEIIKDIVDPKKLGYWAHESTFKRAKYLRQKTYIQD

IYAKEVDGKLIECSPDEATTTKFSVKCAGMTDTIKKKVTFDNFRVGFSST

GKPKPVQVNGGVVLVDSVFTIK

SEQ ID NO: 3
MSRKMFSCDFETTTKLDDCRVWAYGYMEIGNLDNYKIGNSLDEFMQWVME

IQADLYFHNLKFDGAFIVNWLEQHGFKWSNEGLPNTYNTIISKMGQWYMI

DICFGYKGKRKLHTVIYDSLKKLPFPVKKIAKDFQLPLLKGDIDYHTERP

VGHEITPEEYEYIKNDIEIIARALDIQFKQGLDRMTAGSDSLKGFKDILS

TKKFNKVFPKLSLPMDKEIRKAYRGGFTWLNDKYKEKEIGEGMVFDVNSL

YPSQMYSRPLPYGAPIVFQGKYEKDEQYPLYIQRIRFEFELKEGYIPTIQ

-continued

```
IKKNPFFKGNEYLKNSGVEPVELYLTNVDLELIQEHYELYNVEYIDGFKF
REKTGLFKDFIDKWTYVKTHEEGAKKQLAKLMLNSLYGKFASNPDVTGKV
PYLKDDGSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYVKEVDGKLKECSPDEATTTKFSVKCAGMTDTIKKKVTFDNFAVGFSSM
GKPKPVQVNGGVVLVDSVFTIK
```

SEQ ID NO: 4
```
MSRKMFSCDFETTTKLDDCRVWAYGYMEIGNLDNYKIGNSLDEFMQWVME
IQADLYFHNLKFDGAFIVNWLEQHGFKWSNEGLPNTYNTIISKMGQWYMI
DICFGYRGKRKLHTVIYDSLKKLPFPVKKIAKDFQLPLLKGDIDYHTERP
VGHEITPEEYEYIKNDIEIIARALDIQFKQGLDRMTAGSDSLKGFKDILS
TKKFNKVFPKLSLPMDKEIRKAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGVEPVELYLTNVDLELIQEHYELYNVEYIDGFKF
REKTGLFKDFIDKWTYVKTHEEGAKKQLAKLMLNSLYGKFASNPDVTGKV
PYLKDDGSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYVKEVDGKLKECSPDEATTTKFSVKCAGMTDTIKKKVTFDNFAVGFSSM
GKPKPVQVNGGVVLVDSVFTIK
```
Mutant
                                    SEQ ID NO: 5
```
MPRKMFSCDFETTTKLDDCRVWAYGYMEIGNLDNYKIGNSLDEFMQWVME
IQADLYFHNLKFDGAFIVNWLERHGFKWSNEGLPNTYNTIISKMGQWYMID
ICFGYKGKRKLHTVIYDSLKKLPFPVKKIAKDFQLPLLKGDIDYHKERPV
GHEITPEEYEYIKNDIEIIARALDIQFKQGLDRMTAGSDSLKGFKDILST
KKFNKVFPKLSLPMDKEIRAYRGGFTWLNDKYKEKEIGEGMVFDVNSLY
PSQMYSRPLPYGAPIVFQGKYEKDEQYPLYIQRIRFEFELKEGYIPTIQI
KKNPFFKGNEYLKNSGGEPVELYLTNVDLELIQEHYELYNVEYIDGFKFR
EKTGLFKDFIDKWTYVKTHEEGAKKQLAKLMLNSLYGKFASNPDVTGKVP
YLKEDGSLGFRVGDEEYKDPVYTPMGVFITAWARFTTITAAQACYDRIIY
CDTDSIHLTGTEVPEIIKDIVDPKKLGYWAHESTFKRAKYLRQKTYIQDI
YMKEVDGKLVECSPDEATTTKFSVKCAGMTDTIKKKVTFDNFKVGFSSKG
KPKPVQVNGGVVLVDSVFTIK
```
Mutant
                                    SEQ ID NO: 6
```
MPRKMFSCDFETTTKLDDCRVWAYGYMEIGNLDNYKIGNSLDEFMQWVME
IQADLYFHNLKFDGAFIVNWLEHNGFKWSNEGLPNTYNTIISKMGQWYMI
DICFGYKGKRKLHTVIYDSLKKLPFPVKKIAKDFQLPLLKGDIDYHKERP
VGHEITPEEYEYIKNDIEIIARALDIQFKQGLDRMTAGSDSLKGFKDILS
TKKFNKVFPKLSLPMDKEIRYAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGGEPVELYLTNVDLELIQEHYELYNVEYIDGFKF
REKTGLFKDFIDKWTYVKTHEEGAKKQLAKLMLNSLYGKFASNPDVTGKV
PYLKEDGSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYMKEVDGKLVECSPDEATTTKFSVKCAGMTDTIKKKVTFDNFKVGFSRS
GKPKPVQVNGGVVLVDSVFTIK
```
Mutant
                                    SEQ ID NO: 7
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHKERP
VGHEITPEEYEYIKNDIEIIARALDIQFKQGLDRMTAGSDSLKGFKDILS
TKKFNKVFPKLSLPMDKEIRQAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGEEPVELYLTNVDLELIQEHYEVYNVEYIDGFKF
REKTGLFKNFIDKWTYVKTHENGAKKQLAKLMLDSLYGKFASNPDVTGKV
PYLKEDGSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYKKEVDGKLGECSPDEATTTKFSVKCAGMTDTIKKKVTFDNFQVGFSSN
GKPKPVQVNGGVVLVDSVFTIK
```
Mutant
                                    SEQ ID NO: 8
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHIERP
VGHEITPEEYEYIKNDIEIIARALDIQFKQGLDRMTAGSDSLKGFKDILS
TKKFNKVFPKLSLPMDKEIRQAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGTEPVELYLTNVDLELIQEHYEIYNVEYIDGFKF
REKTGLFKTFIDKWTYVKTHENGAKKQLAKLMLFDSLYGKFASNPDVTGKV
PYLKEDGSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYKKEVDGKLRECSPDEATTTKFSVKCAGMTDTIKKKVTFDNFQVGFSSK
GKPKPVQVNGGVVLVDSVFTIK
```
Mutant
                                    SEQ ID NO: 9
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHEERP
VGHEITPEEYEYIKNDIEIIARALDIQFKQGLDRMTAGSDSLKGFKDILS
TKKFNKVFPKLSLPMDKEIRQAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGGEPVELYLTNVDLELIQEHYEIYNVEYIDGFKF
REKTGLFKTFIDKWTYVKTHETGAKKQLAKLMLFDSLYGKFASNPDVTGKV
PYLKEDGSLGFRVGDEEYKDPVYTPMGVFITAWARFTTITAAQACYDRII
```

-continued

```
YCDTDSIHLTGTEVPEIIKDIVDPKKLGYWAHESTFKRAKYLRQKTYIQD
IYGKEVDGKLDECSPDEATTTKFSVKCAGMTDTIKKKVTFDNFKVGFSSK
GKPKPVQVNGGVVLVDSVFTIK
```

Mutant SEQ ID NO: 10
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHGERP
VGHEITPEEYEYIKNDIEIIARALDIQFKQGLDRMTAGSDSLKGFKDILS
TKKFNKVFPKLSLPMDKEIRHAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGNEPVELYLTNVDLELIQEHYEIYNVEYIDGFKF
REKTGLFKTFIDKWTYVKTHENGAKKQLAKLMFDSLYGKFASNPDVTGKV
PYLKEDSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYKKEVDGKLRECSPDEATTTKFSVKCAGMTDTIKKKVTFDNFEVGFSSD
GKPKPVQVNGGVVLVDSVFTIK
```

Mutant SEQ ID NO: 11
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHKERP
VGHEITPEEYEYIKNDIEIIARALDIQFKQGLDRMTAGSDSLKGFKDILS
TKKFNKVFPKLSLPMDKEIRHAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGDEPVELYLTNVDLELIQEHYELYNVEYIDGFKF
REKTGLFKNFIDKWTYVKTHETGAKKQLAKLMFDSLYGKFASNPDVTGKV
PYLKEDSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYKKEVDGKLGECSPDEATTTKFSVKCAGMTDTIKKKVTFDNFDVGFSSS
GKPKPVQVNGGVVLVDSVFTIK
```

Mutant SEQ ID NO: 12
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHGERP
VGHEITPEEYEYIKNDIEIIARALDIQFKQGLDRMTAGSDSLKGFKDILS
TKKFNKVFPKLSLPMDKEIRHAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGNEPVELYLTNVDLELIQEHYEIYNVEYIDGFKF
REKTGLFKTFIDKWTYVKTHEEGAKKQLAKLMFDSLYGKFASNPDVTGKV
PYLKEDSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYMKEVDGKLRECSPDEATTTKFSVKCAGMTDTIKKKVTFDNFEVGFSSS
GKPKPVQVNGGVVLVDSVFTIK
```

Mutant SEQ ID NO: 13
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHYERP
VGHEITPEEYEYIKNDIEIIARALDIQFKQGLDRMTAGSDSLKGFKDILS
TKKFNKVFPKLSLPMDKEIRGAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGDEPVELYLTNVDLELIQEHYEVYNVEYIDGFKF
REKTGLFKNFIDKWTYVKTHETGAKKQLAKLMFDSLYGKFASNPDVTGKV
PYLKEDSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYKKEVDGKLVECSPDEATTTKFSVKCAGMTDTIKKKVTFDNFKVGFSSE
GKPKPVQVNGGVVLVDSVFTIK
```

Mutant SEQ ID NO: 14
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHYERP
VGHEITPEEYEYIKNDIEIIARALDIQFKQGLDRMTAGSDSLKGFKDILS
TKKFNKVFPKLSLPMDKEIRGAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGTEPVELYLTNVDLELIQEHYEIYNVEYIDGFKF
REKTGLFKNFIDKWTYVKTHETGAKKQLAKLMFDSLYGKFASNPDVTGKV
PYLKEDSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYKKEVDGKLRECSPDEATTTKFSVKCAGMTDTIKKKVTFDNFHVGFSSK
GKPKPVQVNGGVVLVDSVFTIK
```

Mutant SEQ ID NO: 15
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHGERP
VGHEITPEEYEYIKNDIEIIARALDIQFKQGLDRMTAGSDSLKGFKDILS
TKKFNKVFPKLSLPMDKEIREAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGTEPVELYLTNVDLELIQEHYELYNVEYIDGFKF
REKTGLFKNFIDKWTYVKTHENGAKKQLAKLMFDSLYGKFASNPDVTGKV
PYLKEDSLGFRVGDEEYKDPVYTPMGVFITAWARFTTITAAQACYDRII
```

-continued
```
YCDTDSIHLTGTEVPEIIKDIVDPKKLGYWAHESTFKRAKYLRQKTYIQD
IYKKEVDGKLRECSPDEATTTKFSVKCAGMTDTIKKKVTFDNFHVGFSSK
GKPKPVQVNGGVVLVDSVFTIK
```

Mutant SEQ ID NO: 16
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHKERP
VGHEITPEEYEYIKNDIEIIARALDIQFKQGLDRMTAGSDSLKGFKDILS
TKKFNKVFPKLSLPMDKEIRAAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGEEPVELYLTNVDLELIQEHYEIYNVEYIDGFKF
REKTGLFKQFIDKWTYVKTHEEGAKKQLAKLMFDSLYGKFASNPDVTGKV
PYLKEDGSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYMKEVDGKLGECSPDEATTTKFSVKCAGMTDTIKKKVTFDNFDVGFSSK
GKPKPVQVNGGVVLVDSVFTIK
```

Mutant SEQ ID NO: 17
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHYERP
VGHEITPEEYEYIKNDIEIIARALDIQFKQGLDRMTAGSDSLKGFKDILS
TKKFNKVFPKLSLPMDKEIRQAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGDEPVELYLTNVDLELIQEHYELYNVEYIDGFKF
REKTGLFKDFIDKWTYVKTHETGAKKQLAKLMFDSLYGKFASNPDVTGKV
PYLKEDGSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYGKEVDGKLVECSPDEATTTKFSVKCAGMTDTIKKKVTFDNFDVGFSSD
GKPKPVQVNGGVVLVDSVFTIK
```

Mutant SEQ ID NO: 18
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHYERP
VGHEITPEEYEYIKNDIEIIARALDIQFKQGLDRMTAGSDSLKGFKDILS
TKKFNKVFPKLSLPMDKEIRAAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGEEPVELYLTNVDLELIQEHYELYNVEYIDGFKF
REKTGLFKNFIDKWTYVKTHEEGAKKQLAKLMFDSLYGKFASNPDVTGKV
PYLKEDGSLGFRVGDEEYKDPVYTPMGVFITAWARFTTITAAQACYDRII
```

-continued
```
YCDTDSIHLTGTEVPEIIKDIVDPKKLGYWAHESTFKRAKYLRQKTYIQD
IYMKEVDGKLVECSPDEATTTKFSVKCAGMTDTIKKKVTFDNFNVGFSSN
GKPKPVQVNGGVVLVDSVFTIK
```

Mutant SEQ ID NO: 19
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHIERP
VGHEITPEEYEYIKNDIEIIARALDIQFKQGLDRMTAGSDSLKGFKDILS
TKKFNKVFPKLSLPMDKEIRHAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGGEPVELYLTNVDLELIQEHYEVYNVEYIDGFKF
REKTGLFKNFIDKWTYVKTHENGAKKQLAKLMFDSLYGKFASNPDVTGKV
PYLKEDGSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYMKEVDGKLGECSPDEATTTKFSVKCAGMTDTIKKKVTFDNFKVGFSSN
GKPKPVQVNGGVVLVDSVFTIK
```

Mutant SEQ ID NO: 20
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHIERP
VGHEITPEEYEYIKNDIEIIARALDIQFKQGLDRMTAGSDSLKGFKDILS
TKKFNKVFPKLSLPMDKEIRAAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGGEPVELYLTNVDLELIQEHYEIYNVEYIDGFKF
REKTGLFKTFIDKWTYVKTHENGAKKQLAKLMFDSLYGKFASNPDVTGKV
PYLKEDGSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYMKEVDGKLDECSPDEATTTKFSVKCAGMTDTIKKKVTFDNFNVGFSSS
GKPKPVQVNGGVVLVDSVFTIK
```

Mutant SEQ ID NO: 21
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHGERP
VGHEITPEEYEYIKNDIEIIARALDIQFKQGLDRMTAGSDSLKGFKDILS
TKKFNKVFPKLSLPMDKEIRHAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGDEPVELYLTNVDLELIQEHYELYNVEYIDGFKF
REKTGLFKNFIDKWTYVKTHENGAKKQLAKLMFDSLYGKFASNPDVTGKV
PYLKEDGSLGFRVGDEEYKDPVYTPMGVFITAWARFTTITAAQACYDRII
```

-continued

```
YCDTDSIHLTGTEVPEIIKDIVDPKKLGYWAHESTFKRAKYLRQKTYIQD
IYMKEVDGKLGECSPDEATTTKFSVKCAGMTDTIKKKVTFDNFQVGFSSD
GKPKPVQVNGGVVLVDSVFTIK
```

Mutant  
SEQ ID NO: 22
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHIERP
VGHEITPEEYEYIKNDIEIIARALDIQFKQGLDRMTAGSDSLKGFKDILS
TKKFNKVFPKLSLPMDKEIRYAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGDEPVELYLTNVDLELIQEHYEVYNVEYIDGFKF
REKTGLFKNFIDKWTYVKTHETGAKKQLAKLMFDSLYGKFASNPDVTGKV
PYLKEDGSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYMKEVDGKLDECSPDEATTTKFSVKCAGMTDTIKKKVTFDNFHVGFSSN
GKPKPVQVNGGVVLVDSVFTIK
```

Mutant  
SEQ ID NO: 23
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHIERP
VGHEITPEEYEYIKNDIEIIARALDIQFKQGLDRMTAGSDSLKGFKDILS
TKKFNKVFPKLSLPMDKEIRGAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGEEPVELYLTNVDLELIQEHYELYNVEYIDGFKF
REKTGLFKTFIDKWTYVKTHETGAKKQLAKLMFDSLYGKFASNPDVTGKV
PYLKEDGSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYGKEVDGKLGECSPDEATTTKFSVKCAGMTDTIKKKVTFDNFEVGFSSN
GKPKPVQVNGGVVLVDSVFTIK
```

Mutant  
SEQ ID NO: 24
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHEERP
VGHEITPEEYEYIKNDIEIIARALDIQFKQGLDRMTAGSDSLKGFKDILS
TKKFNKVFPKLSLPMDKEIRHAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGGEPVELYLTNVDLELIQEHYEVYNVEYIDGFKF
REKTGLFKDFIDKWTYVKTHETGAKKQLAKLMFDSLYGKFASNPDVTGKV
PYLKEDGSLGFRVGDEEYKDPVYTPMGVFITAWARFTTITAAQACYDRII
```

-continued

```
YCDTDSIHLTGTEVPEIIKDIVDPKKLGYWAHESTFKRAKYLRQKTYIQD
IYGKEVDGKLDECSPDEATTTKFSVKCAGMTDTIKKKVTFDNFDVGFSSD
GKPKPVQVNGGVVLVDSVFTIK
```

Mutant  
SEQ ID NO: 25
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHEERP
VGHEITPEEYEYIKNDIEIIARALDIQFKQGLDRMTAGSDSLKGFKDILS
TKKFNKVFPKLSLPMDKEIRAAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGTEPVELYLTNVDLELIQEHYEIYNVEYIDGFKF
REKTGLFKNFIDKWTYVKTHENGAKKQLAKLMFDSLYGKFASNPDVTGKV
PYLKEDGSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYGKEVDGKLDECSPDEATTTKFSVKCAGMTDTIKKKVTFDNFQVGFSSN
GKPKPVQVNGGVVLVDSVFTIK
```

Mutant  
SEQ ID NO: 26
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHIERP
VGHEITPEEYEYIKNDIEIIARALDIQFKQGLDRMTAGSDSLKGFKDILS
TKKFNKVFPKLSLPMDKEIRNAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGTEPVELYLTNVDLELIQEHYEVYNVEYIDGFKF
REKTGLFKNFIDKWTYVKTHETGAKKQLAKLMFDSLYGKFASNPDVTGKV
PYLKEDGSLGFRVGDEEYKDPVYTPMGVFITAWARFTTITAAQACYDRII
YCDTDSIHLTGTEVPEIIKDIVDPKKLGYWAHESTFKRAKYLRQKTYIQD
IYGKEVDGKLVECSPDEATTTKFSVKCAGMTDTIKKKVTFDNFEVGFSSK
GKPKPVQVNGGVVLVDSVFTIK
```

Mutant  
SEQ ID NO: 27
```
MPRKMFSCDFETTTKLDDCRVWAYGYMEIGNLDNYKIGNSLDEFMQWVME
IQADLYFHNLKFDGAFIVNWLEHHGFKWSNEGLPNTYNTIISKMGQWYMI
DICFGYKGKRKLHTVIYDSLKKLPFPVKKIAKDFQLPLLKGDIDYHEERP
VGHEITPEEYEYIKNDIEIIARALDIQFKQGLDRMTAGSDSLKGFKDILS
TKKFNKVFPKLSLPMDKEIRHAYRGGFTWLNDKYKEKEIGEGMVFDVNSL
YPSQMYSRPLPYGAPIVFQGKYEKDEQYPLYIQRIRFEFELKEGYIPTIQ
IKKNPFFKGNEYLKNSGDEPVELYLTNVDLELIQEHYEVYNVEYIDGFKF
REKTGLFKTFIDKWTYVKTHETGAKKQLAKLMFDSLYGKFASNPDVTGKV
```

-continued

PYLKEDGSLGFRVGDEEYKDPVYTPMGVFITAWARFTTITAAQACYDRII

YCDTDSIHLTGTEVPEIIKDIVDPKKLGYWAHESTFKRAKYLRQKTYIQD

IYMKEVDGKLVECSPDEATTTKFSVKCAGMTDTIKKKVTFDNFNVGFSSE

GKPKPVQVNGGVVLVDSVFTIK

---

What is claimed is:

1. A DNA polymerase comprising an amino acid sequence that has at least 95% sequence identity with SEQ ID NO:2 and at least one amino acid substitution selected from the group consisting of: A147K, R221Y, A318G, A503M, I511V, R544K and T550K.

2. The DNA polymerase according to claim 1, further comprising at least 2 amino acid substitutions selected from the group consisting of: A147K, R221Y, A318G, A503M, I511V, R544K and T550K.

3. The DNA polymerase according to claim 1, further comprising at least 3 amino acid substitutions selected from the group consisting of: A147K, R221Y, A318G, A503M, I511V, R544K and T550K.

4. The DNA polymerase according to claim 1, further comprising at least 4 amino acid substitutions selected from the group consisting of: A147K, R221Y, A318G, A503M, I511V, R544K and T550K.

5. The DNA polymerase according to claim 1, further comprising at least 5 amino acid substitutions selected from the group consisting of: A147K, R221Y, A318G, A503M, I511V, R544K and T550K.

6. The DNA polymerase according to claim 1, further comprising at least 6 amino acid substitutions selected from the group consisting of: A147K, R221Y, A318G, A503M, I511V, R544K and T550K.

7. The DNA polymerase according to claim 1, further comprising 7 amino acid substitution that consist of A147K, R221Y, A318G, A503M, I511V, R544K and T550K.

8. The DNA polymerase according to claim 1, further comprising substitutions at one or more positions selected from 339, 359, 383 and 384.

9. The DNA polymerase according to claim 1, wherein the DNA polymerase is a fusion protein.

10. A DNA polymerase composition comprising at least 99% sequence identity with SEQ ID NO:5.

11. A kit comprising:
(i) the DNA polymerase according to claim 1; and
(ii) a reaction buffer.

12. The kit of claim 11, wherein the DNA polymerase is lyophilized and/or the reaction buffer is in concentrated form.

13. The kit of claim 11, further comprising one or more primers.

14. The kit of claim 13, whereon the primers are selected from the group consisting of: random primers, exonuclease-resistant primers and primers having chemical modifications.

15. The kit of claim 1, further comprising one or more dNTPs, crowding agents and/or cationic, anionic, zwitterionic or non-ionic detergents.

16. A method for improved isothermal amplification of a target DNA, comprising:
preparing a reaction mix comprising the target DNA with a DNA polymerase of claim 1, dNTPs and, optionally, one or more primers; and amplifying the target DNA isothermally.

17. The method according to claim 16, further comprising amplifying the target DNA at an amplification temperature in the range of 30° C.-42° C.

18. The method according to claim 16, wherein the target DNA is linear or circular.

19. The method according to claim 16, wherein the target DNA is a whole genome or a target DNA sequence therein.

20. The method according to claim 16, further comprising amplifying the target DNA at a temperature in the range of 30° C.-42° C.; and obtaining a higher yield within 2 hours of amplified DNA compared to the yield obtained with wild-type Phi29 DNA polymerase under the same reaction conditions.

21. The method according to claim 16, further comprising amplifying the target DNA at a temperature in the range of 30° C.-42° C. and obtaining a higher rate of amplification compared to the rate of amplification using wild-type Phi29 DNA polymerase under the same reaction conditions.

22. The method according to claim 16, further comprising amplifying the target DNA at a temperature in the range of 30° C.-42° C. and obtaining a more even representation of the substrate DNA compared to the biased representation of wild-type Phi29 DNA polymerase under the same reaction conditions.

23. The method according to claim 16, further comprising amplifying the target DNA at a temperature in the range of 30° C.-42° C., and obtaining reduced background compared to amplifying the substrate DNA with wild-type Phi29 DNA polymerase under the same reaction conditions.

24. The method according to claim 16, further comprising amplifying the target DNA in a high salt buffer.

\* \* \* \* \*

SEQUENCE LISTING

<160> NUMBER OF SEQ ID NOS: 27

<210> SEQ ID NO 1
<211> LENGTH: 572
<212> TYPE: PRT
<213> ORGANISM: Artificial Sequence
<220> FEATURE:
<223> OTHER INFORMATION: Synthetic construct

<400> SEQUENCE: 1

```
Met Pro Arg Lys Met Tyr Ser Cys Asp Phe Glu Thr Thr Thr Lys Val
1               5                   10                  15

Glu Asp Cys Arg Val Trp Ala Tyr Gly Tyr Met Asn Ile Glu Asp His
            20                  25                  30

Ser Glu Tyr Lys Ile Gly Asn Ser Leu Asp Glu Phe Met Ala Trp Val
        35                  40                  45

Leu Lys Val Gln Ala Asp Leu Tyr Phe His Asn Leu Lys Phe Asp Gly
    50                  55                  60

Ala Phe Ile Ile Asn Trp Leu Glu Arg Asn Gly Phe Lys Trp Ser Ala
65                  70                  75                  80

Asp Gly Leu Pro Asn Thr Tyr Asn Thr Ile Ile Ser Arg Met Gly Gln
                85                  90                  95

Trp Tyr Met Ile Asp Ile Cys Leu Gly Tyr Lys Gly Lys Arg Lys Ile
            100                 105                 110

His Thr Val Ile Tyr Asp Ser Leu Lys Lys Leu Pro Phe Pro Val Lys
        115                 120                 125

Lys Ile Ala Lys Asp Phe Lys Leu Thr Val Leu Lys Gly Asp Ile Asp
    130                 135                 140

Tyr His Lys Glu Arg Pro Val Gly Tyr Lys Ile Thr Pro Glu Glu Tyr
145                 150                 155                 160

Ala Tyr Ile Lys Asn Asp Ile Gln Ile Ile Ala Glu Ala Leu Leu Ile
                165                 170                 175

Gln Phe Lys Gln Gly Leu Asp Arg Met Thr Ala Gly Ser Asp Ser Leu
            180                 185                 190

Lys Gly Phe Lys Asp Ile Ile Thr Thr Lys Lys Phe Lys Lys Val Phe
        195                 200                 205

Pro Thr Leu Ser Leu Gly Leu Asp Lys Glu Val Arg Tyr Ala Tyr Arg
    210                 215                 220

Gly Gly Phe Thr Trp Leu Asn Asp Arg Phe Lys Glu Lys Glu Ile Gly
225                 230                 235                 240

Glu Gly Met Val Phe Asp Val Asn Ser Leu Tyr Pro Ala Gln Met Tyr
                245                 250                 255

Ser Arg Leu Leu Pro Tyr Gly Glu Pro Ile Val Phe Glu Gly Lys Tyr
            260                 265                 270

Val Trp Asp Glu Asp Tyr Pro Leu His Ile Gln His Ile Arg Cys Glu
        275                 280                 285

Phe Glu Leu Lys Glu Gly Tyr Ile Pro Thr Ile Gln Ile Lys Arg Ser
    290                 295                 300

Arg Phe Tyr Lys Gly Asn Glu Tyr Leu Lys Ser Ser Gly Gly Glu Ile
305                 310                 315                 320
```

```
Ala Asp Leu Trp Leu Ser Asn Val Asp Leu Glu Leu Met Lys Glu His
            325                 330                 335

Tyr Asp Leu Tyr Asn Val Glu Tyr Ile Ser Gly Leu Lys Phe Lys Ala
        340                 345                 350

Thr Thr Gly Leu Phe Lys Asp Phe Ile Asp Lys Trp Thr Tyr Ile Lys
    355                 360                 365

Thr Thr Ser Glu Gly Ala Ile Lys Gln Leu Ala Lys Leu Met Leu Asn
370                 375                 380

Ser Leu Tyr Gly Lys Phe Ala Ser Asn Pro Asp Val Thr Gly Lys Val
385                 390                 395                 400

Pro Tyr Leu Lys Glu Asn Gly Ala Leu Gly Phe Arg Leu Gly Glu Glu
                405                 410                 415

Glu Thr Lys Asp Pro Val Tyr Thr Pro Met Gly Val Phe Ile Thr Ala
            420                 425                 430

Trp Ala Arg Tyr Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Ile
    450                 455                 460

Pro Asp Val Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Met Lys Glu Val Asp Gly Lys Leu Val Glu
            500                 505                 510

Gly Ser Pro Asp Asp Tyr Thr Asp Ile Lys Phe Ser Val Lys Cys Ala
        515                 520                 525

Gly Met Thr Asp Lys Ile Lys Lys Glu Val Thr Phe Glu Asn Phe Lys
    530                 535                 540

Val Gly Phe Ser Arg Lys Met Lys Pro Lys Pro Val Gln Val Pro Gly
545                 550                 555                 560

Gly Val Val Leu Val Asp Asp Thr Phe Thr Ile Lys
                565                 570

<210> SEQ ID NO 2
<211> LENGTH: 572
<212> TYPE: PRT
<213> ORGANISM: Artificial Sequence
<220> FEATURE:
<223> OTHER INFORMATION: Synthetic construct

<400> SEQUENCE: 2

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110
```

```
His Thr Val Ile Tyr Asp Ser Leu Lys Lys Leu Pro Phe Pro Val Lys
            115                 120                 125
Lys Ile Ala Lys Asp Phe Gln Leu Pro Leu Leu Lys Gly Asp Ile Asp
130                 135                 140
Tyr His Ala Glu Arg Pro Val Gly His Glu Ile Thr Pro Glu Glu Tyr
145                 150                 155                 160
Glu Tyr Ile Lys Asn Asp Ile Glu Ile Ala Arg Ala Leu Asp Ile
                165                 170                 175
Gln Phe Lys Gln Gly Leu Asp Arg Met Thr Ala Gly Ser Asp Ser Leu
                180                 185                 190
Lys Gly Phe Lys Asp Ile Leu Ser Thr Lys Lys Phe Asn Lys Val Phe
            195                 200                 205
Pro Lys Leu Ser Leu Pro Met Asp Lys Glu Ile Arg Arg Ala Tyr Arg
            210                 215                 220
Gly Gly Phe Thr Trp Leu Asn Asp Lys Tyr Lys Glu Lys Glu Ile Gly
225                 230                 235                 240
Glu Gly Met Val Phe Asp Val Asn Ser Leu Tyr Pro Ser Gln Met Tyr
                245                 250                 255
Ser Arg Pro Leu Pro Tyr Gly Ala Pro Ile Val Phe Gln Gly Lys Tyr
            260                 265                 270
Glu Lys Asp Glu Gln Tyr Pro Leu Tyr Ile Gln Arg Ile Arg Phe Glu
            275                 280                 285
Phe Glu Leu Lys Glu Gly Tyr Ile Pro Thr Ile Gln Ile Lys Lys Asn
            290                 295                 300
Pro Phe Phe Lys Gly Asn Glu Tyr Leu Lys Asn Ser Gly Ala Glu Pro
305                 310                 315                 320
Val Glu Leu Tyr Leu Thr Asn Val Asp Leu Glu Leu Ile Gln Glu His
                325                 330                 335
Tyr Glu Met Tyr Asn Val Glu Tyr Ile Asp Gly Phe Lys Phe Arg Glu
            340                 345                 350
Lys Thr Gly Leu Phe Lys Glu Phe Ile Asp Lys Trp Thr Tyr Val Lys
            355                 360                 365
Thr His Glu Lys Gly Ala Lys Lys Gln Leu Ala Lys Leu Met Phe Asp
            370                 375                 380
Ser Leu Tyr Gly Lys Phe Ala Ser Asn Pro Asp Val Thr Gly Lys Val
385                 390                 395                 400
Pro Tyr Leu Lys Glu Asp Gly Ser Leu Gly Phe Arg Val Gly Asp Glu
                405                 410                 415
Glu Tyr Lys Asp Pro Val Tyr Thr Pro Met Gly Val Phe Ile Thr Ala
                420                 425                 430
Trp Ala Arg Phe Thr Thr Ile Thr Ala Ala Gln Ala Cys Tyr Asp Arg
            435                 440                 445
Ile Ile Tyr Cys Asp Thr Asp Ser Ile His Leu Thr Gly Thr Glu Val
            450                 455                 460
Pro Glu Ile Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
                485                 490                 495
Tyr Ile Gln Asp Ile Tyr Ala Lys Glu Val Asp Gly Lys Leu Ile Glu
                500                 505                 510
Cys Ser Pro Asp Glu Ala Thr Thr Lys Phe Ser Val Lys Cys Ala
            515                 520                 525
```

```
Gly Met Thr Asp Thr Ile Lys Lys Val Thr Phe Asp Asn Phe Arg
        530             535             540
Val Gly Phe Ser Ser Thr Gly Lys Pro Lys Pro Val Gln Val Asn Gly
545                 550             555                 560
Gly Val Val Leu Val Asp Ser Val Phe Thr Ile Lys
            565             570
```

<210> SEQ ID NO 3
<211> LENGTH: 572
<212> TYPE: PRT
<213> ORGANISM: Artificial Sequence
<220> FEATURE:
<223> OTHER INFORMATION: Synthetic construct

<400> SEQUENCE: 3

```
Met Ser Arg Lys Met Phe Ser Cys Asp Phe Glu Thr Thr Lys Leu
1               5                   10                  15
Asp Asp Cys Arg Val Trp Ala Tyr Gly Tyr Met Glu Ile Gly Asn Leu
                20                  25                  30
Asp Asn Tyr Lys Ile Gly Asn Ser Leu Asp Glu Phe Met Gln Trp Val
            35                  40                  45
Met Glu Ile Gln Ala Asp Leu Tyr Phe His Asn Leu Lys Phe Asp Gly
50                  55                  60
Ala Phe Ile Val Asn Trp Leu Glu Gln His Gly Phe Lys Trp Ser Asn
65                  70                  75                  80
Glu Gly Leu Pro Asn Thr Tyr Asn Thr Ile Ser Lys Met Gly Gln
                85                  90                  95
Trp Tyr Met Ile Asp Ile Cys Phe Gly Tyr Lys Gly Lys Arg Lys Leu
                100                 105                 110
His Thr Val Ile Tyr Asp Ser Leu Lys Lys Leu Pro Phe Pro Val Lys
            115                 120                 125
Lys Ile Ala Lys Asp Phe Gln Leu Pro Leu Leu Lys Gly Asp Ile Asp
            130                 135                 140
Tyr His Thr Glu Arg Pro Val Gly His Glu Ile Thr Pro Glu Glu Tyr
145                 150                 155                 160
Glu Tyr Ile Lys Asn Asp Ile Glu Ile Ile Ala Arg Ala Leu Asp Ile
                165                 170                 175
Gln Phe Lys Gln Gly Leu Asp Arg Met Thr Ala Gly Ser Asp Ser Leu
                180                 185                 190
Lys Gly Phe Lys Asp Ile Leu Ser Thr Lys Lys Phe Asn Lys Val Phe
            195                 200                 205
Pro Lys Leu Ser Leu Pro Met Asp Lys Glu Ile Arg Lys Ala Tyr Arg
210                 215                 220
Gly Gly Phe Thr Trp Leu Asn Asp Lys Tyr Lys Glu Lys Glu Ile Gly
225                 230                 235                 240
Glu Gly Met Val Phe Asp Val Asn Ser Leu Tyr Pro Ser Gln Met Tyr
                245                 250                 255
Ser Arg Pro Leu Pro Tyr Gly Ala Pro Ile Val Phe Gln Gly Lys Tyr
                260                 265                 270
Glu Lys Asp Glu Gln Tyr Pro Leu Tyr Ile Gln Arg Ile Arg Phe Glu
            275                 280                 285
Phe Glu Leu Lys Glu Gly Tyr Ile Pro Thr Ile Gln Ile Lys Lys Asn
            290                 295                 300
Pro Phe Phe Lys Gly Asn Glu Tyr Leu Lys Asn Ser Gly Val Glu Pro
305                 310                 315                 320
```

Val Glu Leu Tyr Leu Thr Asn Val Asp Leu Glu Leu Ile Gln Glu His
            325                 330                 335

Tyr Glu Leu Tyr Asn Val Glu Tyr Ile Asp Gly Phe Lys Phe Arg Glu
            340                 345                 350

Lys Thr Gly Leu Phe Lys Asp Phe Ile Asp Lys Trp Thr Tyr Val Lys
            355                 360                 365

Thr His Glu Glu Gly Ala Lys Lys Gln Leu Ala Lys Leu Met Leu Asn
            370                 375                 380

Ser Leu Tyr Gly Lys Phe Ala Ser Asn Pro Asp Val Thr Gly Lys Val
385                 390                 395                 400

Pro Tyr Leu Lys Asp Asp Gly Ser Leu Gly Phe Arg Val Gly Asp Glu
            405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
            450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
            485                 490                 495

Tyr Ile Gln Asp Ile Tyr Val Lys Glu Val Asp Gly Lys Leu Lys Glu
            500                 505                 510

Cys Ser Pro Asp Glu Ala Thr Thr Thr Lys Phe Ser Val Lys Cys Ala
            515                 520                 525

Gly Met Thr Asp Thr Ile Lys Lys Lys Val Thr Phe Asp Asn Phe Ala
            530                 535                 540

Val Gly Phe Ser Ser Met Gly Lys Pro Lys Pro Val Gln Val Asn Gly
545                 550                 555                 560

Gly Val Val Leu Val Asp Ser Val Phe Thr Ile Lys
            565                 570

<210> SEQ ID NO 4
<211> LENGTH: 572
<212> TYPE: PRT
<213> ORGANISM: Artificial Sequence
<220> FEATURE:
<223> OTHER INFORMATION: Synthetic construct

<400> SEQUENCE: 4

Met Ser Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
            50                  55                  60

Ala Phe Ile Val Asn Trp Leu Glu Gln His Gly Phe Lys Trp Ser Asn
65                  70                  75                  80

Glu Gly Leu Pro Asn Thr Tyr Asn Thr Ile Ile Ser Lys Met Gly Gln
            85                  90                  95

Trp Tyr Met Ile Asp Ile Cys Phe Gly Tyr Arg Gly Lys Arg Lys Leu
            100                 105                 110

```
His Thr Val Ile Tyr Asp Ser Leu Lys Lys Leu Pro Phe Pro Val Lys
            115                 120                 125

Lys Ile Ala Lys Asp Phe Gln Leu Pro Leu Leu Lys Gly Asp Ile Asp
130                 135                 140

Tyr His Thr Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
195                 200                 205

Pro Lys Leu Ser Leu Pro Met Asp Lys Glu Ile Arg Lys Ala Tyr Arg
210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Val Glu Pro
305                 310                 315                 320

Val Glu Leu Tyr Leu Thr Asn Val Asp Leu Glu Leu Ile Gln Glu His
                325                 330                 335

Tyr Glu Leu Tyr Asn Val Glu Tyr Ile Asp Gly Phe Lys Phe Arg Glu
            340                 345                 350

Lys Thr Gly Leu Phe Lys Asp Phe Ile Asp Lys Trp Thr Tyr Val Lys
355                 360                 365

Thr His Glu Glu Gly Ala Lys Lys Gln Leu Ala Lys Leu Met Leu Asn
370                 375                 380

Ser Leu Tyr Gly Lys Phe Ala Ser Asn Pro Asp Val Thr Gly Lys Val
385                 390                 395                 400

Pro Tyr Leu Lys Asp Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Val Lys Glu Val Asp Gly Lys Leu Lys Glu
            500                 505                 510

Cys Ser Pro Asp Glu Ala Thr Thr Thr Lys Phe Ser Val Lys Cys Ala
515                 520                 525

Gly Met Thr Asp Thr Ile Lys Lys Lys Val Thr Phe Asp Asn Phe Ala
```

```
            530                 535                 540
Val Gly Phe Ser Ser Met Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 5
<211> LENGTH: 572
<212> TYPE: PRT
<213> ORGANISM: Artificial Sequence
<220> FEATURE:
<223> OTHER INFORMATION: Syntheitc construct

<400> SEQUENCE: 5

Met Pro Arg Lys Met Phe Ser Cys Asp Phe Glu Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
                35                  40                  45

Met Glu Ile Gln Ala Asp Leu Tyr Phe His Asn Leu Lys Phe Asp Gly
50                  55                  60

Ala Phe Ile Val Asn Trp Leu Glu Arg His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
                100                 105                 110

His Thr Val Ile Tyr Asp Ser Leu Lys Lys Leu Pro Phe Pro Val Lys
                115                 120                 125

Lys Ile Ala Lys Asp Phe Gln Leu Pro Leu Leu Lys Gly Asp Ile Asp
                130                 135                 140

Tyr His Lys Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
                180                 185                 190

Lys Gly Phe Lys Asp Ile Leu Ser Thr Lys Lys Phe Asn Lys Val Phe
                195                 200                 205

Pro Lys Leu Ser Leu Pro Met Asp Lys Glu Ile Arg Tyr Ala Tyr Arg
                210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
                260                 265                 270

Glu Lys Asp Glu Gln Tyr Pro Leu Tyr Ile Gln Arg Ile Arg Phe Glu
                275                 280                 285

Phe Glu Leu Lys Glu Gly Tyr Ile Pro Thr Ile Gln Ile Lys Lys Asn
                290                 295                 300

Pro Phe Phe Lys Gly Asn Glu Tyr Leu Lys Asn Ser Gly Gly Glu Pro
305                 310                 315                 320

Val Glu Leu Tyr Leu Thr Asn Val Asp Leu Glu Leu Ile Gln Glu His
```

```
              325                 330                 335
Tyr Glu Leu Tyr Asn Val Glu Tyr Ile Asp Gly Phe Lys Phe Arg Glu
            340                 345                 350
Lys Thr Gly Leu Phe Lys Asp Phe Ile Asp Lys Trp Thr Tyr Val Lys
            355                 360                 365
Thr His Glu Glu Gly Ala Lys Lys Gln Leu Ala Lys Leu Met Leu Asn
            370                 375                 380
Ser Leu Tyr Gly Lys Phe Ala Ser Asn Pro Asp Val Thr Gly Lys Val
385                 390                 395                 400
Pro Tyr Leu Lys Glu Asp Gly Ser Leu Gly Phe Arg Val Gly Asp Glu
                405                 410                 415
Glu Tyr Lys Asp Pro Val Tyr Thr Pro Met Gly Val Phe Ile Thr Ala
            420                 425                 430
Trp Ala Arg Phe Thr Thr Ile Thr Ala Ala Gln Ala Cys Tyr Asp Arg
            435                 440                 445
Ile Ile Tyr Cys Asp Thr Asp Ser Ile His Leu Thr Gly Thr Glu Val
            450                 455                 460
Pro Glu Ile Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
                485                 490                 495
Tyr Ile Gln Asp Ile Tyr Met Lys Glu Val Asp Gly Lys Leu Val Glu
                500                 505                 510
Cys Ser Pro Asp Glu Ala Thr Thr Thr Lys Phe Ser Val Lys Cys Ala
            515                 520                 525
Gly Met Thr Asp Thr Ile Lys Lys Lys Val Thr Phe Asp Asn Phe Lys
            530                 535                 540
Val Gly Phe Ser Ser Lys Gly Lys Pro Lys Pro Val Gln Val Asn Gly
545                 550                 555                 560
Gly Val Val Leu Val Asp Ser Val Phe Thr Ile Lys
                565                 570

<210> SEQ ID NO 6
<211> LENGTH: 572
<212> TYPE: PRT
<213> ORGANISM: Artificial Sequence
<220> FEATURE:
<223> OTHER INFORMATION: Synthetic construct

<400> SEQUENCE: 6

Met Pro Arg Lys Met Phe Ser Cys Asp Phe Glu Thr Thr Thr Lys Leu
1               5                   10                  15
Asp Asp Cys Arg Val Trp Ala Tyr Gly Tyr Met Glu Ile Gly Asn Leu
                20                  25                  30
Asp Asn Tyr Lys Ile Gly Asn Ser Leu Asp Glu Phe Met Gln Trp Val
            35                  40                  45
Met Glu Ile Gln Ala Asp Leu Tyr Phe His Asn Leu Lys Phe Asp Gly
        50                  55                  60
Ala Phe Ile Val Asn Trp Leu Glu His Asn Gly Phe Lys Trp Ser Asn
65                  70                  75                  80
Glu Gly Leu Pro Asn Thr Tyr Asn Thr Ile Ile Ser Lys Met Gly Gln
                85                  90                  95
Trp Tyr Met Ile Asp Ile Cys Phe Gly Tyr Lys Gly Lys Arg Lys Leu
                100                 105                 110
His Thr Val Ile Tyr Asp Ser Leu Lys Lys Leu Pro Phe Pro Val Lys
```

-continued

```
            115                 120                 125
Lys Ile Ala Lys Asp Phe Gln Leu Pro Leu Leu Lys Gly Asp Ile Asp
            130                 135                 140
Tyr His Lys Glu Arg Pro Val Gly His Glu Ile Thr Pro Glu Glu Tyr
145                 150                 155                 160
Glu Tyr Ile Lys Asn Asp Ile Glu Ile Ala Arg Ala Leu Asp Ile
                165                 170                 175
Gln Phe Lys Gln Gly Leu Asp Arg Met Thr Ala Gly Ser Asp Ser Leu
                180                 185                 190
Lys Gly Phe Lys Asp Ile Leu Ser Thr Lys Lys Phe Asn Lys Val Phe
            195                 200                 205
Pro Lys Leu Ser Leu Pro Met Asp Lys Glu Ile Arg Tyr Ala Tyr Arg
210                 215                 220
Gly Gly Phe Thr Trp Leu Asn Asp Lys Tyr Lys Glu Lys Glu Ile Gly
225                 230                 235                 240
Glu Gly Met Val Phe Asp Val Asn Ser Leu Tyr Pro Ser Gln Met Tyr
                245                 250                 255
Ser Arg Pro Leu Pro Tyr Gly Ala Pro Ile Val Phe Gln Gly Lys Tyr
            260                 265                 270
Glu Lys Asp Glu Gln Tyr Pro Leu Tyr Ile Gln Arg Ile Arg Phe Glu
            275                 280                 285
Phe Glu Leu Lys Glu Gly Tyr Ile Pro Thr Ile Gln Ile Lys Lys Asn
290                 295                 300
Pro Phe Phe Lys Gly Asn Glu Tyr Leu Lys Asn Ser Gly Gly Glu Pro
305                 310                 315                 320
Val Glu Leu Tyr Leu Thr Asn Val Asp Leu Glu Leu Ile Gln Glu His
                325                 330                 335
Tyr Glu Leu Tyr Asn Val Glu Tyr Ile Asp Gly Phe Lys Phe Arg Glu
                340                 345                 350
Lys Thr Gly Leu Phe Lys Asp Phe Ile Asp Lys Trp Thr Tyr Val Lys
            355                 360                 365
Thr His Glu Glu Gly Ala Lys Lys Gln Leu Ala Lys Leu Met Leu Asn
            370                 375                 380
Ser Leu Tyr Gly Lys Phe Ala Ser Asn Pro Asp Val Thr Gly Lys Val
385                 390                 395                 400
Pro Tyr Leu Lys Glu Asp Gly Ser Leu Gly Phe Arg Val Gly Asp Glu
                405                 410                 415
Glu Tyr Lys Asp Pro Val Tyr Thr Pro Met Gly Val Phe Ile Thr Ala
                420                 425                 430
Trp Ala Arg Phe Thr Thr Ile Thr Ala Ala Gln Ala Cys Tyr Asp Arg
            435                 440                 445
Ile Ile Tyr Cys Asp Thr Asp Ser Ile His Leu Thr Gly Thr Glu Val
            450                 455                 460
Pro Glu Ile Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
                485                 490                 495
Tyr Ile Gln Asp Ile Tyr Met Lys Glu Val Asp Gly Lys Leu Val Glu
                500                 505                 510
Cys Ser Pro Asp Glu Ala Thr Thr Thr Lys Phe Ser Val Lys Cys Ala
            515                 520                 525
Gly Met Thr Asp Thr Ile Lys Lys Lys Val Thr Phe Asp Asn Phe Lys
            530                 535                 540
```

Val Gly Phe Ser Arg Ser Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 7
<211> LENGTH: 572
<212> TYPE: PRT
<213> ORGANISM: Artificial Sequence
<220> FEATURE:
<223> OTHER INFORMATION: Synthetic construct

<400> SEQUENCE: 7

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
        50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
130                 135                 140

Tyr His Lys Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Gly Ala Tyr Arg
210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Glu Glu Pro
305                 310                 315                 320

Val Glu Leu Tyr Leu Thr Asn Val Asp Leu Glu Leu Ile Gln Glu His
                325                 330                 335

```
Tyr Glu Val Tyr Asn Val Glu Tyr Ile Asp Gly Phe Lys Phe Arg Glu
                340                 345                 350

Lys Thr Gly Leu Phe Lys Asn Phe Ile Asp Lys Trp Thr Tyr Val Lys
            355                 360                 365

Thr His Glu Asn Gly Ala Lys Lys Gln Leu Ala Lys Leu Met Phe Asp
        370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
        450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Lys Lys Glu Val Asp Gly Lys Leu Gly Glu
            500                 505                 510

Cys Ser Pro Asp Glu Ala Thr Thr Thr Lys Phe Ser Val Lys Cys Ala
        515                 520                 525

Gly Met Thr Asp Thr Ile Lys Lys Lys Val Thr Phe Asp Asn Phe Gln
        530                 535                 540

Val Gly Phe Ser Ser Asn Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 8
<211> LENGTH: 572
<212> TYPE: PRT
<213> ORGANISM: Artificial Sequence
<220> FEATURE:
<223> OTHER INFORMATION: Synthetic construct

<400> SEQUENCE: 8

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
        50                  55                  60

Ala Phe Ile Val Asn Trp Leu Glu His His Gly Phe Lys Trp Ser Asn
65              70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125
```

```
Lys Ile Ala Lys Asp Phe Gln Leu Pro Leu Leu Lys Gly Asp Ile Asp
            130                 135                 140

Tyr His Ile Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
            195                 200                 205

Pro Lys Leu Ser Leu Pro Met Asp Lys Glu Ile Arg Gln Ala Tyr Arg
        210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
                260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
        290                 295                 300

Pro Phe Phe Lys Gly Asn Glu Tyr Leu Lys Asn Ser Gly Thr Glu Pro
305                 310                 315                 320

Val Glu Leu Tyr Leu Thr Asn Val Asp Leu Glu Leu Ile Gln Glu His
                325                 330                 335

Tyr Glu Ile Tyr Asn Val Glu Tyr Ile Asp Gly Phe Lys Phe Arg Glu
                340                 345                 350

Lys Thr Gly Leu Phe Lys Thr Phe Ile Asp Lys Trp Thr Tyr Val Lys
            355                 360                 365

Thr His Glu Asn Gly Ala Lys Lys Gln Leu Ala Lys Leu Met Phe Asp
        370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
        450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Lys Lys Glu Val Asp Gly Lys Leu Arg Glu
            500                 505                 510

Cys Ser Pro Asp Glu Ala Thr Thr Thr Lys Phe Ser Val Lys Cys Ala
        515                 520                 525

Gly Met Thr Asp Thr Ile Lys Lys Lys Val Thr Phe Asp Asn Phe Gln
530                 535                 540
```

-continued

Val Gly Phe Ser Ser Lys Gly Lys Pro Lys Pro Val Gln Val Asn Gly
545                 550                 555                 560

Gly Val Val Leu Val Asp Ser Val Phe Thr Ile Lys
            565                 570

<210> SEQ ID NO 9
<211> LENGTH: 572
<212> TYPE: PRT
<213> ORGANISM: Artificial Sequence
<220> FEATURE:
<223> OTHER INFORMATION: Synthetic construct

<400> SEQUENCE: 9

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
                100                 105                 110

His Thr Val Ile Tyr Asp Ser Leu Lys Lys Leu Pro Phe Pro Val Lys
            115                 120                 125

Lys Ile Ala Lys Asp Phe Gln Leu Pro Leu Leu Lys Gly Asp Ile Asp
    130                 135                 140

Tyr His Glu Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
    195                 200                 205

Pro Lys Leu Ser Leu Pro Met Asp Lys Glu Ile Arg Gln Ala Tyr Arg
210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
    275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Gly Glu Pro
305                 310                 315                 320

Val Glu Leu Tyr Leu Thr Asn Val Asp Leu Glu Leu Ile Gln Glu His
                325                 330                 335

```
Tyr Glu Ile Tyr Asn Val Glu Tyr Ile Asp Gly Phe Lys Phe Arg Glu
                340                 345                 350

Lys Thr Gly Leu Phe Lys Thr Phe Ile Asp Lys Trp Thr Tyr Val Lys
            355                 360                 365

Thr His Glu Thr Gly Ala Lys Lys Gln Leu Ala Lys Leu Met Phe Asp
        370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Gly Lys Glu Val Asp Gly Lys Leu Asp Glu
            500                 505                 510

Cys Ser Pro Asp Glu Ala Thr Thr Lys Phe Ser Val Lys Cys Ala
        515                 520                 525

Gly Met Thr Asp Thr Ile Lys Lys Lys Val Thr Phe Asp Asn Phe Lys
530                 535                 540

Val Gly Phe Ser Ser Lys Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 10
<211> LENGTH: 572
<212> TYPE: PRT
<213> ORGANISM: Artificial Sequence
<220> FEATURE:
<223> OTHER INFORMATION: Synthetic construct

<400> SEQUENCE: 10

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
        50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125
```

-continued

```
Lys Ile Ala Lys Asp Phe Gln Leu Pro Leu Leu Lys Gly Asp Ile Asp
            130                 135                 140

Tyr His Gly Glu Arg Pro Val Gly His Glu Ile Thr Pro Glu Tyr
145                 150                 155                 160

Glu Tyr Ile Lys Asn Asp Ile Glu Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
                195                 200                 205

Pro Lys Leu Ser Leu Pro Met Asp Lys Glu Ile Arg His Ala Tyr Arg
            210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
            290                 295                 300

Pro Phe Phe Lys Gly Asn Glu Tyr Leu Lys Asn Ser Gly Asn Glu Pro
305                 310                 315                 320

Val Glu Leu Tyr Leu Thr Asn Val Asp Leu Glu Leu Ile Gln Glu His
                325                 330                 335

Tyr Glu Ile Tyr Asn Val Glu Tyr Ile Asp Gly Phe Lys Phe Arg Glu
            340                 345                 350

Lys Thr Gly Leu Phe Lys Thr Phe Ile Asp Lys Trp Thr Tyr Val Lys
            355                 360                 365

Thr His Glu Asn Gly Ala Lys Lys Gln Leu Ala Lys Leu Met Phe Asp
            370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
            450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Lys Lys Glu Val Asp Gly Lys Leu Arg Glu
            500                 505                 510

Cys Ser Pro Asp Glu Ala Thr Thr Lys Phe Ser Val Lys Cys Ala
            515                 520                 525

Gly Met Thr Asp Thr Ile Lys Lys Lys Val Thr Phe Asp Asn Phe Glu
530                 535                 540

Val Gly Phe Ser Ser Asp Gly Lys Pro Lys Pro Val Gln Val Asn Gly
```

```
                545                 550                 555                 560
Gly Val Val Leu Val Asp Ser Val Phe Thr Ile Lys
                    565                 570

<210> SEQ ID NO 11
<211> LENGTH: 572
<212> TYPE: PRT
<213> ORGANISM: Artificial Sequence
<220> FEATURE:
<223> OTHER INFORMATION: Synthetic construct

<400> SEQUENCE: 11

Met Pro Arg Lys Met Phe Ser Cys Asp Phe Glu Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
                35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                    85                  90                  95

Trp Tyr Met Ile Asp Ile Cys Phe Gly Tyr Lys Gly Lys Arg Lys Leu
                100                 105                 110

His Thr Val Ile Tyr Asp Ser Leu Lys Lys Leu Pro Phe Pro Val Lys
            115                 120                 125

Lys Ile Ala Lys Asp Phe Gln Leu Pro Leu Leu Lys Gly Asp Ile Asp
130                 135                 140

Tyr His Lys Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg His Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Asp Glu Pro
305                 310                 315                 320

Val Glu Leu Tyr Leu Thr Asn Val Asp Leu Glu Leu Ile Gln Glu His
                325                 330                 335

Tyr Glu Leu Tyr Asn Val Glu Tyr Ile Asp Gly Phe Lys Phe Arg Glu
```

```
                 340                 345                 350
Lys Thr Gly Leu Phe Lys Asn Phe Ile Asp Lys Trp Thr Tyr Val Lys
            355                 360                 365

Thr His Glu Thr Gly Ala Lys Lys Gln Leu Ala Lys Leu Met Phe Asp
        370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Lys Lys Glu Val Asp Gly Lys Leu Gly Glu
            500                 505                 510

Cys Ser Pro Asp Glu Ala Thr Thr Lys Phe Ser Val Lys Cys Ala
        515                 520                 525

Gly Met Thr Asp Thr Ile Lys Lys Lys Val Thr Phe Asp Asn Phe Asp
    530                 535                 540

Val Gly Phe Ser Ser Gly Lys Pro Lys Pro Val Gln Val Asn Gly
545                 550                 555                 560

Gly Val Val Leu Val Asp Ser Val Phe Thr Ile Lys
                565                 570
```

<210> SEQ ID NO 12
<211> LENGTH: 572
<212> TYPE: PRT
<213> ORGANISM: Artificial Sequence
<220> FEATURE:
<223> OTHER INFORMATION: Synthetic construct

<400> SEQUENCE: 12

```
Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
```

```
            130                 135                 140
Tyr His Gly Glu Arg Pro Val Gly His Glu Ile Thr Pro Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
                180                 185                 190

Lys Gly Phe Lys Asp Ile Leu Ser Thr Lys Lys Phe Asn Lys Val Phe
                195                 200                 205

Pro Lys Leu Ser Leu Pro Met Asp Lys Glu Ile Arg His Ala Tyr Arg
                210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
                260                 265                 270

Glu Lys Asp Glu Gln Tyr Pro Leu Tyr Ile Gln Arg Ile Arg Phe Glu
                275                 280                 285

Phe Glu Leu Lys Glu Gly Tyr Ile Pro Thr Ile Gln Ile Lys Lys Asn
                290                 295                 300

Pro Phe Phe Lys Gly Asn Glu Tyr Leu Lys Asn Ser Gly Asn Glu Pro
305                 310                 315                 320

Val Glu Leu Tyr Leu Thr Asn Val Asp Leu Glu Leu Ile Gln Glu His
                325                 330                 335

Tyr Glu Ile Tyr Asn Val Glu Tyr Ile Asp Gly Phe Lys Phe Arg Glu
                340                 345                 350

Lys Thr Gly Leu Phe Lys Thr Phe Ile Asp Lys Trp Thr Tyr Val Lys
                355                 360                 365

Thr His Glu Glu Gly Ala Lys Lys Gln Leu Ala Lys Leu Met Phe Asp
                370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
                420                 425                 430

Trp Ala Arg Phe Thr Thr Ile Thr Ala Ala Gln Ala Cys Tyr Asp Arg
                435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Met Lys Glu Val Asp Gly Lys Leu Arg Glu
                500                 505                 510

Cys Ser Pro Asp Glu Ala Thr Thr Thr Lys Phe Ser Val Lys Cys Ala
                515                 520                 525

Gly Met Thr Asp Thr Ile Lys Lys Lys Val Thr Phe Asp Asn Phe Glu
530                 535                 540

Val Gly Phe Ser Ser Ser Gly Lys Pro Lys Pro Val Gln Val Asn Gly
545                 550                 555                 560
```

-continued

```
Gly Val Val Leu Val Asp Ser Val Phe Thr Ile Lys
            565                 570

<210> SEQ ID NO 13
<211> LENGTH: 572
<212> TYPE: PRT
<213> ORGANISM: Artificial Sequence
<220> FEATURE:
<223> OTHER INFORMATION: Synthetic construct

<400> SEQUENCE: 13

Met Pro Arg Lys Met Phe Ser Cys Asp Phe Glu Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
                35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
                100                 105                 110

His Thr Val Ile Tyr Asp Ser Leu Lys Lys Leu Pro Phe Pro Val Lys
                115                 120                 125

Lys Ile Ala Lys Asp Phe Gln Leu Pro Leu Leu Lys Gly Asp Ile Asp
        130                 135                 140

Tyr His Tyr Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
                180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Gly Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
                260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Asp Glu Pro
305                 310                 315                 320

Val Glu Leu Tyr Leu Thr Asn Val Asp Leu Glu Leu Ile Gln Glu His
                325                 330                 335

Tyr Glu Val Tyr Asn Val Glu Tyr Ile Asp Gly Phe Lys Phe Arg Glu
                340                 345                 350
```

-continued

```
Lys Thr Gly Leu Phe Lys Asn Phe Ile Asp Lys Trp Thr Tyr Val Lys
            355                 360                 365

Thr His Glu Thr Gly Ala Lys Lys Gln Leu Ala Lys Leu Met Phe Asp
        370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
                420                 425                 430

Trp Ala Arg Phe Thr Thr Ile Thr Ala Ala Gln Ala Cys Tyr Asp Arg
                435                 440                 445

Ile Ile Tyr Cys Asp Thr Asp Ser Ile His Leu Thr Gly Thr Glu Val
                450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Lys Lys Glu Val Asp Gly Lys Leu Val Glu
                500                 505                 510

Cys Ser Pro Asp Glu Ala Thr Thr Thr Lys Phe Ser Val Lys Cys Ala
                515                 520                 525

Gly Met Thr Asp Thr Ile Lys Lys Lys Val Thr Phe Asp Asn Phe Lys
                530                 535                 540

Val Gly Phe Ser Ser Glu Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 14
<211> LENGTH: 572
<212> TYPE: PRT
<213> ORGANISM: Artificial Sequence
<220> FEATURE:
<223> OTHER INFORMATION: Synthetic construct

<400> SEQUENCE: 14

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
        50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
                100                 105                 110

His Thr Val Ile Tyr Asp Ser Leu Lys Lys Leu Pro Phe Pro Val Lys
            115                 120                 125

Lys Ile Ala Lys Asp Phe Gln Leu Pro Leu Leu Lys Gly Asp Ile Asp
        130                 135                 140
```

-continued

```
Tyr His Tyr Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
            165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
            195                 200                 205

Pro Lys Leu Ser Leu Pro Met Asp Lys Glu Ile Arg Gly Ala Tyr Arg
            210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Thr Glu Pro
305                 310                 315                 320

Val Glu Leu Tyr Leu Thr Asn Val Asp Leu Glu Leu Ile Gln Glu His
                325                 330                 335

Tyr Glu Ile Tyr Asn Val Glu Tyr Ile Asp Gly Phe Lys Phe Arg Glu
                340                 345                 350

Lys Thr Gly Leu Phe Lys Asn Phe Ile Asp Lys Trp Thr Tyr Val Lys
            355                 360                 365

Thr His Glu Thr Gly Ala Lys Lys Gln Leu Ala Lys Leu Met Phe Asp
            370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
            450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Lys Lys Glu Val Asp Gly Lys Leu Arg Glu
            500                 505                 510

Cys Ser Pro Asp Glu Ala Thr Thr Thr Lys Phe Ser Val Lys Cys Ala
            515                 520                 525

Gly Met Thr Asp Thr Ile Lys Lys Lys Val Thr Phe Asp Asn Phe His
            530                 535                 540

Val Gly Phe Ser Ser Lys Gly Lys Pro Lys Pro Val Gln Val Asn Gly
545                 550                 555                 560
```

```
Gly Val Val Leu Val Asp Ser Val Phe Thr Ile Lys
            565                 570
```

<210> SEQ ID NO 15
<211> LENGTH: 572
<212> TYPE: PRT
<213> ORGANISM: Artificial Sequence
<220> FEATURE:
<223> OTHER INFORMATION: Synthetic construct

<400> SEQUENCE: 15

```
Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Gly Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Glu Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Thr Glu Pro
305                 310                 315                 320

Val Glu Leu Tyr Leu Thr Asn Val Asp Leu Glu Leu Ile Gln Glu His
                325                 330                 335

Tyr Glu Leu Tyr Asn Val Glu Tyr Ile Asp Gly Phe Lys Phe Arg Glu
            340                 345                 350
```

```
Lys Thr Gly Leu Phe Lys Asn Phe Ile Asp Lys Trp Thr Tyr Val Lys
            355                 360                 365

Thr His Glu Asn Gly Ala Lys Lys Gln Leu Ala Lys Leu Met Phe Asp
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Lys Lys Glu Val Asp Gly Lys Leu Arg Glu
            500                 505                 510

Cys Ser Pro Asp Glu Ala Thr Thr Lys Phe Ser Val Lys Cys Ala
        515                 520                 525

Gly Met Thr Asp Thr Ile Lys Lys Val Thr Phe Asp Asn Phe His
    530                 535                 540

Val Gly Phe Ser Ser Lys Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 16
<211> LENGTH: 572
<212> TYPE: PRT
<213> ORGANISM: Artificial Sequence
<220> FEATURE:
<223> OTHER INFORMATION: Synthetic construct

<400> SEQUENCE: 16

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140
```

```
Tyr His Lys Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
            165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Phe Asn Lys Val Phe
            195                 200                 205

Pro Lys Leu Ser Leu Pro Met Asp Lys Glu Ile Arg Ala Ala Tyr Arg
            210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Glu Glu Pro
305                 310                 315                 320

Val Glu Leu Tyr Leu Thr Asn Val Asp Leu Glu Leu Ile Gln Glu His
                325                 330                 335

Tyr Glu Ile Tyr Asn Val Glu Tyr Ile Asp Gly Phe Lys Phe Arg Glu
                340                 345                 350

Lys Thr Gly Leu Phe Lys Gln Phe Ile Asp Lys Trp Thr Tyr Val Lys
            355                 360                 365

Thr His Glu Glu Gly Ala Lys Lys Gln Leu Ala Lys Leu Met Phe Asp
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
            405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
            450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
            485                 490                 495

Tyr Ile Gln Asp Ile Tyr Met Lys Glu Val Asp Gly Lys Leu Gly Glu
            500                 505                 510

Cys Ser Pro Asp Glu Ala Thr Thr Lys Phe Ser Val Lys Cys Ala
            515                 520                 525

Gly Met Thr Asp Thr Ile Lys Lys Lys Val Thr Phe Asp Asn Phe Asp
            530                 535                 540

Val Gly Phe Ser Ser Lys Gly Lys Pro Lys Pro Val Gln Val Asn Gly
545                 550                 555                 560

Gly Val Val Leu Val Asp Ser Val Phe Thr Ile Lys
```

<210> SEQ ID NO 17
<211> LENGTH: 572
<212> TYPE: PRT
<213> ORGANISM: Artificial Sequence
<220> FEATURE:
<223> OTHER INFORMATION: Synthetic construct

<400> SEQUENCE: 17

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
130                 135                 140

Tyr His Tyr Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Gln Ala Tyr Arg
210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Asp Glu Pro
305                 310                 315                 320

Val Glu Leu Tyr Leu Thr Asn Val Asp Leu Glu Leu Ile Gln Glu His
                325                 330                 335

Tyr Glu Leu Tyr Asn Val Glu Tyr Ile Asp Gly Phe Lys Phe Arg Glu
            340                 345                 350

Lys Thr Gly Leu Phe Lys Asp Phe Ile Asp Lys Trp Thr Tyr Val Lys

```
              355                 360                 365
Thr His Glu Thr Gly Ala Lys Lys Gln Leu Ala Lys Leu Met Phe Asp
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Gly Lys Glu Val Asp Gly Lys Leu Val Glu
            500                 505                 510

Cys Ser Pro Asp Glu Ala Thr Thr Lys Phe Ser Val Lys Cys Ala
        515                 520                 525

Gly Met Thr Asp Thr Ile Lys Lys Lys Val Thr Phe Asp Asn Phe Asp
530                 535                 540

Val Gly Phe Ser Ser Asp Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 18
<211> LENGTH: 572
<212> TYPE: PRT
<213> ORGANISM: Artificial Sequence
<220> FEATURE:
<223> OTHER INFORMATION: Synthetic construct

<400> SEQUENCE: 18

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
        50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Tyr Glu Arg Pro Val Gly His Glu Ile Thr Pro Glu Glu Tyr
```

```
                145                 150                 155                 160
Glu Tyr Ile Lys Asn Asp Ile Glu Ile Ala Arg Ala Leu Asp Ile
                    165                 170                 175
Gln Phe Lys Gln Gly Leu Asp Arg Met Thr Ala Gly Ser Asp Ser Leu
                    180                 185                 190
Lys Gly Phe Lys Asp Ile Leu Ser Thr Lys Lys Phe Asn Lys Val Phe
                    195                 200                 205
Pro Lys Leu Ser Leu Pro Met Asp Lys Glu Ile Arg Ala Ala Tyr Arg
                    210                 215                 220
Gly Gly Phe Thr Trp Leu Asn Asp Lys Tyr Lys Glu Lys Ile Gly
225                 230                 235                 240
Glu Gly Met Val Phe Asp Val Asn Ser Leu Tyr Pro Ser Gln Met Tyr
                    245                 250                 255
Ser Arg Pro Leu Pro Tyr Gly Ala Pro Ile Val Phe Gln Gly Lys Tyr
                    260                 265                 270
Glu Lys Asp Glu Gln Tyr Pro Leu Tyr Ile Gln Arg Ile Arg Phe Glu
                    275                 280                 285
Phe Glu Leu Lys Glu Gly Tyr Ile Pro Thr Ile Gln Ile Lys Lys Asn
                    290                 295                 300
Pro Phe Phe Lys Gly Asn Glu Tyr Leu Lys Asn Ser Gly Glu Glu Pro
305                 310                 315                 320
Val Glu Leu Tyr Leu Thr Asn Val Asp Leu Glu Leu Ile Gln Glu His
                    325                 330                 335
Tyr Glu Leu Tyr Asn Val Glu Tyr Ile Asp Gly Phe Lys Phe Arg Glu
                    340                 345                 350
Lys Thr Gly Leu Phe Lys Asn Phe Ile Asp Lys Trp Thr Tyr Val Lys
                    355                 360                 365
Thr His Glu Glu Gly Ala Lys Lys Gln Leu Ala Lys Leu Met Phe Asp
                    370                 375                 380
Ser Leu Tyr Gly Lys Phe Ala Ser Asn Pro Asp Val Thr Gly Lys Val
385                 390                 395                 400
Pro Tyr Leu Lys Glu Asp Gly Ser Leu Gly Phe Arg Val Gly Asp Glu
                    405                 410                 415
Glu Tyr Lys Asp Pro Val Tyr Thr Pro Met Gly Val Phe Ile Thr Ala
                    420                 425                 430
Trp Ala Arg Phe Thr Thr Ile Thr Ala Ala Gln Ala Cys Tyr Asp Arg
                    435                 440                 445
Ile Ile Tyr Cys Asp Thr Asp Ser Ile His Leu Thr Gly Thr Glu Val
                    450                 455                 460
Pro Glu Ile Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
                    485                 490                 495
Tyr Ile Gln Asp Ile Tyr Met Lys Glu Val Asp Gly Lys Leu Val Glu
                    500                 505                 510
Cys Ser Pro Asp Glu Ala Thr Thr Lys Phe Ser Val Lys Cys Ala
                    515                 520                 525
Gly Met Thr Asp Thr Ile Lys Lys Val Thr Phe Asp Asn Phe Asn
                    530                 535                 540
Val Gly Phe Ser Ser Asn Gly Lys Pro Lys Pro Val Gln Val Asn Gly
545                 550                 555                 560
Gly Val Val Leu Val Asp Ser Val Phe Thr Ile Lys
                    565                 570
```

-continued

```
<210> SEQ ID NO 19
<211> LENGTH: 572
<212> TYPE: PRT
<213> ORGANISM: Artificial Sequence
<220> FEATURE:
<223> OTHER INFORMATION: Synthetic construct

<400> SEQUENCE: 19

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Ile Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg His Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Gly Glu Pro
305                 310                 315                 320

Val Glu Leu Tyr Leu Thr Asn Val Asp Leu Glu Leu Ile Gln Glu His
                325                 330                 335

Tyr Glu Val Tyr Asn Val Glu Tyr Ile Asp Gly Phe Lys Phe Arg Glu
            340                 345                 350

Lys Thr Gly Leu Phe Lys Asn Phe Ile Asp Lys Trp Thr Tyr Val Lys
        355                 360                 365
```

```
Thr His Glu Asn Gly Ala Lys Lys Gln Leu Ala Lys Leu Met Phe Asp
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
                420                 425                 430

Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Met Lys Glu Val Asp Gly Lys Leu Gly Glu
                500                 505                 510

Cys Ser Pro Asp Glu Ala Thr Thr Thr Lys Phe Ser Val Lys Cys Ala
            515                 520                 525

Gly Met Thr Asp Thr Ile Lys Lys Lys Val Thr Phe Asp Asn Phe Lys
    530                 535                 540

Val Gly Phe Ser Ser Asn Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 20
<211> LENGTH: 572
<212> TYPE: PRT
<213> ORGANISM: Artificial Sequence
<220> FEATURE:
<223> OTHER INFORMATION: Synthetic construct

<400> SEQUENCE: 20

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Ile Glu Arg Pro Val Gly His Glu Ile Thr Pro Glu Glu Tyr
145                 150                 155                 160
```

-continued

Glu Tyr Ile Lys Asn Asp Ile Glu Ile Ile Ala Arg Ala Leu Asp Ile
            165                 170                 175

Gln Phe Lys Gln Gly Leu Asp Arg Met Thr Ala Gly Ser Asp Ser Leu
        180                 185                 190

Lys Gly Phe Lys Asp Ile Leu Ser Thr Lys Lys Phe Asn Lys Val Phe
    195                 200                 205

Pro Lys Leu Ser Leu Pro Met Asp Lys Glu Ile Arg Ala Ala Tyr Arg
210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Gly Glu Pro
305                 310                 315                 320

Val Glu Leu Tyr Leu Thr Asn Val Asp Leu Glu Leu Ile Gln Glu His
                325                 330                 335

Tyr Glu Ile Tyr Asn Val Glu Tyr Ile Asp Gly Phe Lys Phe Arg Glu
            340                 345                 350

Lys Thr Gly Leu Phe Lys Thr Phe Ile Asp Lys Trp Thr Tyr Val Lys
        355                 360                 365

Thr His Glu Asn Gly Ala Lys Lys Gln Leu Ala Lys Leu Met Phe Asp
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Met Lys Glu Val Asp Gly Lys Leu Asp Glu
            500                 505                 510

Cys Ser Pro Asp Glu Ala Thr Thr Lys Phe Ser Val Lys Cys Ala
        515                 520                 525

Gly Met Thr Asp Thr Ile Lys Lys Lys Val Thr Phe Asp Asn Phe Asn
    530                 535                 540

Val Gly Phe Ser Ser Gly Lys Pro Lys Pro Val Gln Val Asn Gly
545                 550                 555                 560

Gly Val Val Leu Val Asp Ser Val Phe Thr Ile Lys
                565                 570

```
<210> SEQ ID NO 21
<211> LENGTH: 572
<212> TYPE: PRT
<213> ORGANISM: Artificial Sequence
<220> FEATURE:
<223> OTHER INFORMATION: Synthetic construct

<400> SEQUENCE: 21

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
130                 135                 140

Tyr His Gly Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg His Ala Tyr Arg
210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Asp Glu Pro
305                 310                 315                 320

Val Glu Leu Tyr Leu Thr Asn Val Asp Leu Glu Leu Ile Gln Glu His
                325                 330                 335

Tyr Glu Leu Tyr Asn Val Glu Tyr Ile Asp Gly Phe Lys Phe Arg Glu
            340                 345                 350

Lys Thr Gly Leu Phe Lys Asn Phe Ile Asp Lys Trp Thr Tyr Val Lys
        355                 360                 365
```

```
Thr His Glu Asn Gly Ala Lys Lys Gln Leu Ala Lys Leu Met Phe Asp
    370                 375                 380
Ser Leu Tyr Gly Lys Phe Ala Ser Asn Pro Asp Val Thr Gly Lys Val
385                 390                 395                 400
Pro Tyr Leu Lys Glu Asp Gly Ser Leu Gly Phe Arg Val Gly Asp Glu
                405                 410                 415
Glu Tyr Lys Asp Pro Val Tyr Thr Pro Met Gly Val Phe Ile Thr Ala
            420                 425                 430
Trp Ala Arg Phe Thr Thr Ile Thr Ala Ala Gln Ala Cys Tyr Asp Arg
                435                 440                 445
Ile Ile Tyr Cys Asp Thr Asp Ser Ile His Leu Thr Gly Thr Glu Val
450                 455                 460
Pro Glu Ile Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
                485                 490                 495
Tyr Ile Gln Asp Ile Tyr Met Lys Glu Val Asp Gly Lys Leu Gly Glu
            500                 505                 510
Cys Ser Pro Asp Glu Ala Thr Thr Thr Lys Phe Ser Val Lys Cys Ala
        515                 520                 525
Gly Met Thr Asp Thr Ile Lys Lys Lys Val Thr Phe Asp Asn Phe Gln
    530                 535                 540
Val Gly Phe Ser Ser Asp Gly Lys Pro Lys Pro Val Gln Val Asn Gly
545                 550                 555                 560
Gly Val Val Leu Val Asp Ser Val Phe Thr Ile Lys
                565                 570

<210> SEQ ID NO 22
<211> LENGTH: 572
<212> TYPE: PRT
<213> ORGANISM: Artificial Sequence
<220> FEATURE:
<223> OTHER INFORMATION: Synthetic construct

<400> SEQUENCE: 22

Met Pro Arg Lys Met Phe Ser Cys Asp Phe Glu Thr Thr Thr Lys Leu
1               5                   10                  15
Asp Asp Cys Arg Val Trp Ala Tyr Gly Tyr Met Glu Ile Gly Asn Leu
                20                  25                  30
Asp Asn Tyr Lys Ile Gly Asn Ser Leu Asp Glu Phe Met Gln Trp Val
            35                  40                  45
Met Glu Ile Gln Ala Asp Leu Tyr Phe His Asn Leu Lys Phe Asp Gly
        50                  55                  60
Ala Phe Ile Val Asn Trp Leu Glu His His Gly Phe Lys Trp Ser Asn
65                  70                  75                  80
Glu Gly Leu Pro Asn Thr Tyr Asn Thr Ile Ile Ser Lys Met Gly Gln
                85                  90                  95
Trp Tyr Met Ile Asp Ile Cys Phe Gly Tyr Lys Gly Lys Arg Lys Leu
            100                 105                 110
His Thr Val Ile Tyr Asp Ser Leu Lys Lys Leu Pro Phe Pro Val Lys
        115                 120                 125
Lys Ile Ala Lys Asp Phe Gln Leu Pro Leu Leu Lys Gly Asp Ile Asp
    130                 135                 140
Tyr His Ile Glu Arg Pro Val Gly His Glu Ile Thr Pro Glu Glu Tyr
145                 150                 155                 160
```

-continued

Glu Tyr Ile Lys Asn Asp Ile Glu Ile Ile Ala Arg Ala Leu Asp Ile
                165                 170                 175
Gln Phe Lys Gln Gly Leu Asp Arg Met Thr Ala Gly Ser Asp Ser Leu
            180                 185                 190
Lys Gly Phe Lys Asp Ile Leu Ser Thr Lys Lys Phe Asn Lys Val Phe
        195                 200                 205
Pro Lys Leu Ser Leu Pro Met Asp Lys Glu Ile Arg Tyr Ala Tyr Arg
    210                 215                 220
Gly Gly Phe Thr Trp Leu Asn Asp Lys Tyr Lys Glu Lys Glu Ile Gly
225                 230                 235                 240
Glu Gly Met Val Phe Asp Val Asn Ser Leu Tyr Pro Ser Gln Met Tyr
                245                 250                 255
Ser Arg Pro Leu Pro Tyr Gly Ala Pro Ile Val Phe Gln Gly Lys Tyr
            260                 265                 270
Glu Lys Asp Glu Gln Tyr Pro Leu Tyr Ile Gln Arg Ile Arg Phe Glu
        275                 280                 285
Phe Glu Leu Lys Glu Gly Tyr Ile Pro Thr Ile Gln Ile Lys Lys Asn
    290                 295                 300
Pro Phe Phe Lys Gly Asn Glu Tyr Leu Lys Asn Ser Gly Asp Glu Pro
305                 310                 315                 320
Val Glu Leu Tyr Leu Thr Asn Val Asp Leu Glu Leu Ile Gln Glu His
                325                 330                 335
Tyr Glu Val Tyr Asn Val Glu Tyr Ile Asp Gly Phe Lys Phe Arg Glu
            340                 345                 350
Lys Thr Gly Leu Phe Lys Asn Phe Ile Asp Lys Trp Thr Tyr Val Lys
        355                 360                 365
Thr His Glu Thr Gly Ala Lys Lys Gln Leu Ala Lys Leu Met Phe Asp
    370                 375                 380
Ser Leu Tyr Gly Lys Phe Ala Ser Asn Pro Asp Val Thr Gly Lys Val
385                 390                 395                 400
Pro Tyr Leu Lys Glu Asp Gly Ser Leu Gly Phe Arg Val Gly Asp Glu
                405                 410                 415
Glu Tyr Lys Asp Pro Val Tyr Thr Pro Met Gly Val Phe Ile Thr Ala
            420                 425                 430
Trp Ala Arg Phe Thr Thr Ile Thr Ala Ala Gln Ala Cys Tyr Asp Arg
        435                 440                 445
Ile Ile Tyr Cys Asp Thr Asp Ser Ile His Leu Thr Gly Thr Glu Val
    450                 455                 460
Pro Glu Ile Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
                485                 490                 495
Tyr Ile Gln Asp Ile Tyr Met Lys Glu Val Asp Gly Lys Leu Asp Glu
            500                 505                 510
Cys Ser Pro Asp Glu Ala Thr Thr Lys Phe Ser Val Lys Cys Ala
        515                 520                 525
Gly Met Thr Asp Thr Ile Lys Lys Lys Val Thr Phe Asp Asn Phe His
    530                 535                 540
Val Gly Phe Ser Ser Asn Gly Lys Pro Lys Pro Val Gln Val Asn Gly
545                 550                 555                 560
Gly Val Val Leu Val Asp Ser Val Phe Thr Ile Lys
                565                 570

<210> SEQ ID NO 23
<211> LENGTH: 572
<212> TYPE: PRT
<213> ORGANISM: Artificial Sequence
<220> FEATURE:
<223> OTHER INFORMATION: Synthetic construct

<400> SEQUENCE: 23

```
Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Ile Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Gly Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Glu Glu Pro
305                 310                 315                 320

Val Glu Leu Tyr Leu Thr Asn Val Asp Leu Glu Leu Ile Gln Glu His
                325                 330                 335

Tyr Glu Leu Tyr Asn Val Glu Tyr Ile Asp Gly Phe Lys Phe Arg Glu
            340                 345                 350

Lys Thr Gly Leu Phe Lys Thr Phe Ile Asp Lys Trp Thr Tyr Val Lys
        355                 360                 365

Thr His Glu Thr Gly Ala Lys Lys Gln Leu Ala Lys Leu Met Phe Asp
```

```
            370                 375                 380
Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Gly Lys Glu Val Asp Gly Lys Leu Gly Glu
            500                 505                 510

Cys Ser Pro Asp Glu Ala Thr Thr Lys Phe Ser Val Lys Cys Ala
        515                 520                 525

Gly Met Thr Asp Thr Ile Lys Lys Val Thr Phe Asp Asn Phe Glu
    530                 535                 540

Val Gly Phe Ser Ser Asn Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 24
<211> LENGTH: 572
<212> TYPE: PRT
<213> ORGANISM: Artificial Sequence
<220> FEATURE:
<223> OTHER INFORMATION: Synthetic construct

<400> SEQUENCE: 24

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Glu Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
```

```
                165                 170                 175
Gln Phe Lys Gln Gly Leu Asp Arg Met Thr Ala Gly Ser Asp Ser Leu
            180                 185                 190

Lys Gly Phe Lys Asp Ile Leu Ser Thr Lys Phe Asn Lys Val Phe
        195                 200                 205

Pro Lys Leu Ser Leu Pro Met Asp Lys Glu Ile Arg His Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Gly Glu Pro
305                 310                 315                 320

Val Glu Leu Tyr Leu Thr Asn Val Asp Leu Glu Leu Ile Gln Glu His
                325                 330                 335

Tyr Glu Val Tyr Asn Val Glu Tyr Ile Asp Gly Phe Lys Phe Arg Glu
            340                 345                 350

Lys Thr Gly Leu Phe Lys Asp Phe Ile Asp Lys Trp Thr Tyr Val Lys
        355                 360                 365

Thr His Glu Thr Gly Ala Lys Lys Gln Leu Ala Lys Leu Met Phe Asp
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Gly Lys Glu Val Asp Gly Lys Leu Asp Glu
            500                 505                 510

Cys Ser Pro Asp Glu Ala Thr Thr Lys Phe Ser Val Lys Cys Ala
        515                 520                 525

Gly Met Thr Asp Thr Ile Lys Lys Lys Val Thr Phe Asp Asn Phe Asp
    530                 535                 540

Val Gly Phe Ser Ser Asp Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 25
```

<211> LENGTH: 572
<212> TYPE: PRT
<213> ORGANISM: Artificial Sequence
<220> FEATURE:
<223> OTHER INFORMATION: Synthetic construct

<400> SEQUENCE: 25

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Glu Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Ala Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Thr Glu Pro
305                 310                 315                 320

Val Glu Leu Tyr Leu Thr Asn Val Asp Leu Glu Leu Ile Gln Glu His
                325                 330                 335

Tyr Glu Ile Tyr Asn Val Glu Tyr Ile Asp Gly Phe Lys Phe Arg Glu
            340                 345                 350

Lys Thr Gly Leu Phe Lys Asn Phe Ile Asp Lys Trp Thr Tyr Val Lys
        355                 360                 365

Thr His Glu Asn Gly Ala Lys Lys Gln Leu Ala Lys Leu Met Phe Asp
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
            405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
            450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
            485                 490                 495

Tyr Ile Gln Asp Ile Tyr Gly Lys Glu Val Asp Gly Lys Leu Asp Glu
            500                 505                 510

Cys Ser Pro Asp Glu Ala Thr Thr Thr Lys Phe Ser Val Lys Cys Ala
            515                 520                 525

Gly Met Thr Asp Thr Ile Lys Lys Lys Val Thr Phe Asp Asn Phe Gln
530                 535                 540

Val Gly Phe Ser Ser Asn Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 26
<211> LENGTH: 572
<212> TYPE: PRT
<213> ORGANISM: Artificial Sequence
<220> FEATURE:
<223> OTHER INFORMATION: Synthetic construct

<400> SEQUENCE: 26

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
            85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Ile Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
            165                 170                 175

```
Gln Phe Lys Gln Gly Leu Asp Arg Met Thr Ala Gly Ser Asp Ser Leu
                180                 185                 190

Lys Gly Phe Lys Asp Ile Leu Ser Thr Lys Lys Phe Asn Lys Val Phe
            195                 200                 205

Pro Lys Leu Ser Leu Pro Met Asp Lys Glu Ile Arg Asn Ala Tyr Arg
        210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
                260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
        290                 295                 300

Pro Phe Phe Lys Gly Asn Glu Tyr Leu Lys Asn Ser Gly Thr Glu Pro
305                 310                 315                 320

Val Glu Leu Tyr Leu Thr Asn Val Asp Leu Glu Leu Ile Gln Glu His
                325                 330                 335

Tyr Glu Val Tyr Asn Val Glu Tyr Ile Asp Gly Phe Lys Phe Arg Glu
                340                 345                 350

Lys Thr Gly Leu Phe Lys Asn Phe Ile Asp Lys Trp Thr Tyr Val Lys
            355                 360                 365

Thr His Glu Thr Gly Ala Lys Lys Gln Leu Ala Lys Leu Met Phe Asp
        370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Gly Lys Glu Val Asp Gly Lys Leu Val Glu
            500                 505                 510

Cys Ser Pro Asp Glu Ala Thr Thr Lys Phe Ser Val Lys Cys Ala
        515                 520                 525

Gly Met Thr Asp Thr Ile Lys Lys Lys Val Thr Phe Asp Asn Phe Glu
        530                 535                 540

Val Gly Phe Ser Ser Lys Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 27
<211> LENGTH: 572
```

```
<212> TYPE: PRT
<213> ORGANISM: Artificial Sequence
<220> FEATURE:
<223> OTHER INFORMATION: Synthetic construct

<400> SEQUENCE: 27

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ser Lys Met Gly Gln
                85                  90                  95

Trp Tyr Met Ile Asp Ile Cys Phe Gly Tyr Lys Gly Lys Arg Lys Leu
                100                 105                 110

His Thr Val Ile Tyr Asp Ser Leu Lys Lys Leu Pro Phe Pro Val Lys
            115                 120                 125

Lys Ile Ala Lys Asp Phe Gln Leu Pro Leu Lys Gly Asp Ile Asp
        130                 135                 140

Tyr His Glu Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg His Ala Tyr Arg
210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
290                 295                 300

Pro Phe Phe Lys Gly Asn Glu Tyr Leu Lys Asn Ser Gly Asp Glu Pro
305                 310                 315                 320

Val Glu Leu Tyr Leu Thr Asn Val Asp Leu Glu Leu Ile Gln Glu His
                325                 330                 335

Tyr Glu Val Tyr Asn Val Glu Tyr Ile Asp Gly Phe Lys Phe Arg Glu
            340                 345                 350

Lys Thr Gly Leu Phe Lys Thr Phe Ile Asp Lys Trp Thr Tyr Val Lys
        355                 360                 365

Thr His Glu Thr Gly Ala Lys Lys Gln Leu Ala Lys Leu Met Phe Asp
    370                 375                 380
```

```
Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Met Lys Glu Val Asp Gly Lys Leu Val Glu
            500                 505                 510

Cys Ser Pro Asp Glu Ala Thr Thr Lys Phe Ser Val Lys Cys Ala
            515                 520                 525

Gly Met Thr Asp Thr Ile Lys Lys Lys Val Thr Phe Asp Asn Phe Asn
        530                 535                 540

Val Gly Phe Ser Ser Glu Gly Lys Pro Lys Pro Val Gln Val Asn Gly
545                 550                 555                 560

Gly Val Val Leu Val Asp Ser Val Phe Thr Ile Lys
                565                 570
```